(12) United States Patent
Cardno et al.

(10) Patent No.: US 10,203,834 B2
(45) Date of Patent: *Feb. 12, 2019

(54) COMPONENT DATA VISUALIZATION METHOD

(71) Applicant: New BIS Safe Luxco S.à r.l, Luxembourg (LU)

(72) Inventors: Andrew John Cardno, San Diego, CA (US); Paul Allan Cardno, Dunedin (NZ); Mukesh Gordhan, San Diego, CA (US)

(73) Assignee: New BIS Safe Luxco S.à.r.l, Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 15/724,064

(22) Filed: Oct. 3, 2017

(65) Prior Publication Data

US 2018/0088711 A1    Mar. 29, 2018

Related U.S. Application Data

(63) Continuation of application No. 13/140,168, filed as application No. PCT/NZ2009/000280 on Dec. 8, 2009, now Pat. No. 9,811,232.

(Continued)

(51) Int. Cl.
*G06F 3/048* (2013.01)
*G06F 8/34* (2018.01)
(Continued)

(52) U.S. Cl.
CPC .............. *G06F 3/048* (2013.01); *G06F 8/34* (2013.01); *G06F 17/30994* (2013.01);
(Continued)

(58) Field of Classification Search
CPC ...... G06F 19/26; G06F 19/20; G06F 17/3061; G06F 17/30994
See application file for complete search history.

(56) References Cited

U.S. PATENT DOCUMENTS

2002/0188424 A1   12/2002   Grinstein et al.
2005/0102316 A1   5/2005    Lawson et al.
(Continued)

OTHER PUBLICATIONS

International Search Report for International Application No. PCT/NZ2009/000280 dated May 6, 2010 (Form PCT/ISA/210).

*Primary Examiner* — Jwalant Amin
(74) *Attorney, Agent, or Firm* — Merchant & Gould P.C.

(57) ABSTRACT

A method of creating a graphical representation of a plurality of components that are grouped in a plurality of component groups, wherein the component groups are formed based on two or more different group types, and values of one or more selectable metrics are associated with the components, the method including the steps of: detecting a selection of the one or more metrics; retrieving metric values for the selected metric associated with components belonging to component groups of a first group type; determining the relative proportion of the retrieved metric values across components that are members of a second type component group; and graphically representing the first type component group using one or more first icons that are graphically represented based on the retrieved metric values, and positioned within a section of the graphical representation based on the determined relative proportion.

18 Claims, 16 Drawing Sheets

Related U.S. Application Data

(60) Provisional application No. 61/138,486, filed on Dec. 17, 2008.

(51) Int. Cl.
*G06T 11/20* (2006.01)
*G06F 17/30* (2006.01)
G06F 19/20 (2011.01)
G06F 19/26 (2011.01)

(52) U.S. Cl.
CPC ........ *G06T 11/206* (2013.01); *G06F 17/3061* (2013.01); *G06F 19/20* (2013.01); *G06F 19/26* (2013.01)

(56) References Cited

U.S. PATENT DOCUMENTS

| | | |
|---|---|---|
| 2005/0179684 A1 | 8/2005 | Wallace |
| 2006/0047617 A1 | 3/2006 | Bacioiu et al. |
| 2007/0011201 A1 | 1/2007 | Subramaniam et al. |
| 2007/0018983 A1 | 1/2007 | Vimme |
| 2007/0300173 A1 | 12/2007 | Woods |
| 2008/0215496 A1 | 9/2008 | Hockley |

Figure 4A — 401

Menu

Lunch Menu July 27th 2008 ▼

| Costs | Revenue | Profit | |
|---|---|---|---|
| $17 | $34 | $17 | Menu Item 1 |
| $2 | $20 | $18 | Menu Item 2 |
| $7.50 | $7.5 | $0 | Menu Item 3 |
| $10 | $25 | $15 | Menu Item 4 |
| $10.30 | $15 | $4.7 | Menu Item 5 |
| $18 | $36 | $18 | Menu Item 6 |
| $26 | $36 | $10 | Menu Item 7 |
| $32 | $50 | $18 | Menu Item 8 |
| $17 | $15 | $2 | Menu Item 9 |
| $ | $ | $ | Menu Item 10 |
| $ | $ | $ | Menu Item 11 |
| $ | $ | $ | Menu Item 12 |
| $ | $ | $ | Menu Item 13 |
| $ | $ | $ | Menu Item 14 |
| $ | $ | $ | Menu Item 15 |
| $ | $ | $ | Menu Item 16 |
| $ | $ | $ | Menu Item 17 |
| $ | $ | $ | Menu Item 18 |
| $ | $ | $ | Menu Item 19 |
| $ | $ | $ | Menu Item 20 |
| $ | $ | $ | Menu Item 21 |
| $ | $ | $ | Menu Item 22 |
| $ | $ | $ | Menu Item 23 |
| $ | $ | $ | Menu Item 24 |
| $ | $ | $ | Menu Item 25 |
| $ | $ | $ | Menu Item 26 |
| $ | $ | $ | Menu Item 27 |
| $ | $ | $ | Menu Item 28 |
| $ | $ | $ | Menu Item 29 |
| $ | $ | $ | Menu Item 30 |
| $ | $ | $ | Menu Item 31 |
| $ | $ | $ | Menu Item 32 |
| $ | $ | $ | Menu Item 33 |
| $ | $ | $ | Menu Item 34 |
| $ | $ | $ | Menu Item 35 |

Fruits

| Costs | |
|---|---|
| $17 | Ingredient 1 |
| $2 | Ingredient 2 |
| $7.50 | Ingredient 3 |
| $10 | Ingredient 4 |
| $10.50 | Ingredient 5 |
| $18 | Ingredient 6 |
| $26 | Ingredient 7 |
| $32 | Ingredient 8 |
| $17 | Ingredient 9 |
| $ | Ingredient 10 |
| $ | Ingredient 11 |
| $ | Ingredient 12 |
| $ | Ingredient 13 |
| $ | Ingredient 14 |
| $ | Ingredient 15 |
| $ | Ingredient 16 |
| $ | Ingredient 17 |
| $ | Ingredient 18 |
| $ | Ingredient 19 |
| $ | Ingredient 20 |
| $ | Ingredient 21 |
| $ | Ingredient 22 |
| $ | Ingredient 23 |
| $ | Ingredient 24 |
| $ | Ingredient 25 |
| $ | Ingredient 26 |
| $ | Ingredient 27 |
| $ | Ingredient 28 |
| $ | Ingredient 29 |
| $ | Ingredient 30 |
| $ | Ingredient 31 |
| $ | Ingredient 32 |
| $ | Ingredient 33 |
| $ | Ingredient 34 |
| $ | Ingredient 35 |
| $ | Ingredient 36 |
|   | Ingredient 37 |
|   | Ingredient 38 |
|   | Ingredient 39 |
|   | Ingredient 40 |
|   | Ingredient 41 |

Figure 4B

COMPONENT DATA VISUALIZATION METHOD

CROSS-REFERENCE TO RELATED APPLICATIONS

This application is a continuation of U.S. application Ser. No. 13/140,168, filed 18 Jan. 2012, which is a National Stage Application of PCT/NZ2009/000280, filed 8 Dec. 2009, which claims benefit of U.S. Provisional Ser. No. 61/138,486, filed 17 Dec. 2008 and which applications are incorporated herein by reference. To the extent appropriate, a claim of priority is made to each of the above disclosed applications.

FIELD OF THE INVENTION

The present invention relates to a component data visualization method, and in particular to a method of creating a graphical representation of a plurality of components that are grouped in a plurality of component groups.

BACKGROUND

A chart or graph is described in Wikipedia as a type of information graphic or graphic organizer that represents tabular numeric data and/or functions. Charts are often used to make it easier to understand large quantities of data and the relationship between different parts of the data. Charts can usually be read more quickly than the raw data that they come from. They are used in a wide variety of fields, and can be created by hand (often on graph paper) or by computer using a charting application.

Traditional charts use well established and often poorly implemented ways of representing data. Many tools exist to help the user construct very sophisticated representations of data but that sophistication typically results in less meaningful charts. Embodiments of the present invention aim to overcome this problem.

It is known to use charting wizards such as those that are available in Excel and various other systems such as those provided by, for example, IBM. In addition there are multiple Business Intelligence (BI) tools available to users to enable users to analyze data in an attempt to create meaningful feedback. However, as the amount of data increases, so does the complexity of the visual representations created by the analysis of the data. These complex representations can end up swamping parts of the visual representation that is most required and relevant to an end user.

One known method of visualizing the components that make up an item being analyzed is to provide a hierarchical table showing how the components contribute to the whole of the item. Also, a bill of materials may be provided to indicate how many of one component are included within the item being analyzed. These lists of information breaking down the constituent components only provide minimal information to a user. These types of list do not provide a detailed representation of how measurements associated with the components correlate when grouping the components according to different grouping mechanisms. In particular, the importance of the components within one group of components with regard to other groups of components is not appreciated.

The present invention aims to overcome, or at least alleviate, some or all of the mentioned problems, or to at least provide the public with a useful choice.

SUMMARY OF THE INVENTION

The present invention provides a system and method that enables visualization of components. The visualization provides easily interpretable information to a user on the relative values of selected metrics according to various component categories.

According to one aspect, the present invention provides a method of creating a graphical representation of a plurality of components that are grouped in a plurality of component groups, wherein the component groups are formed based on two or more different group types, and values of one or more selectable metrics are associated with the components, the method including the steps of: detecting a selection of the one or more metrics; retrieving metric values for the selected metric associated with components belonging to component groups of a first group type; determining the relative proportion of the retrieved metric values across components that are members of a second type component group; and graphically representing the first type component group using one or more first icons that are graphically represented based on the retrieved metric values, and positioned within a section of the graphical representation based on the determined relative proportion.

According to a further aspect, the present invention provides a component data visualization system for creating a graphical representation of a plurality of components that are grouped in a plurality of component groups, wherein the component groups are formed based on two or more different group types, and values of one or more selectable metrics are associated with the components, the system including a selection detection module arranged to detect a selection of the one or more metrics; a data retrieval module arranged to retrieve metric values for the selected metric associated with components belonging to component groups of a first group type from a data storage module in communication with the component data visualization system; a placement module arranged to determine the relative proportion of the retrieved metric values across components that are members of a second type component group; and further arranged to instruct an icon module to graphically represent the first type component group using one or more first icons that are graphically represented based on the retrieved metric values, and position the first icon within a section of the graphical representation based on the determined relative proportion.

BRIEF DESCRIPTION OF THE DRAWINGS

Embodiments of the present invention will now be described, by way of example only, with reference to the accompanying drawings, in which:

FIGS. 4A and 4B show detailed views of the menu items in the graphical representations of FIGS. 1, 2 and 3;

DETAILED DESCRIPTION OF THE INVENTION

Figure 1A:
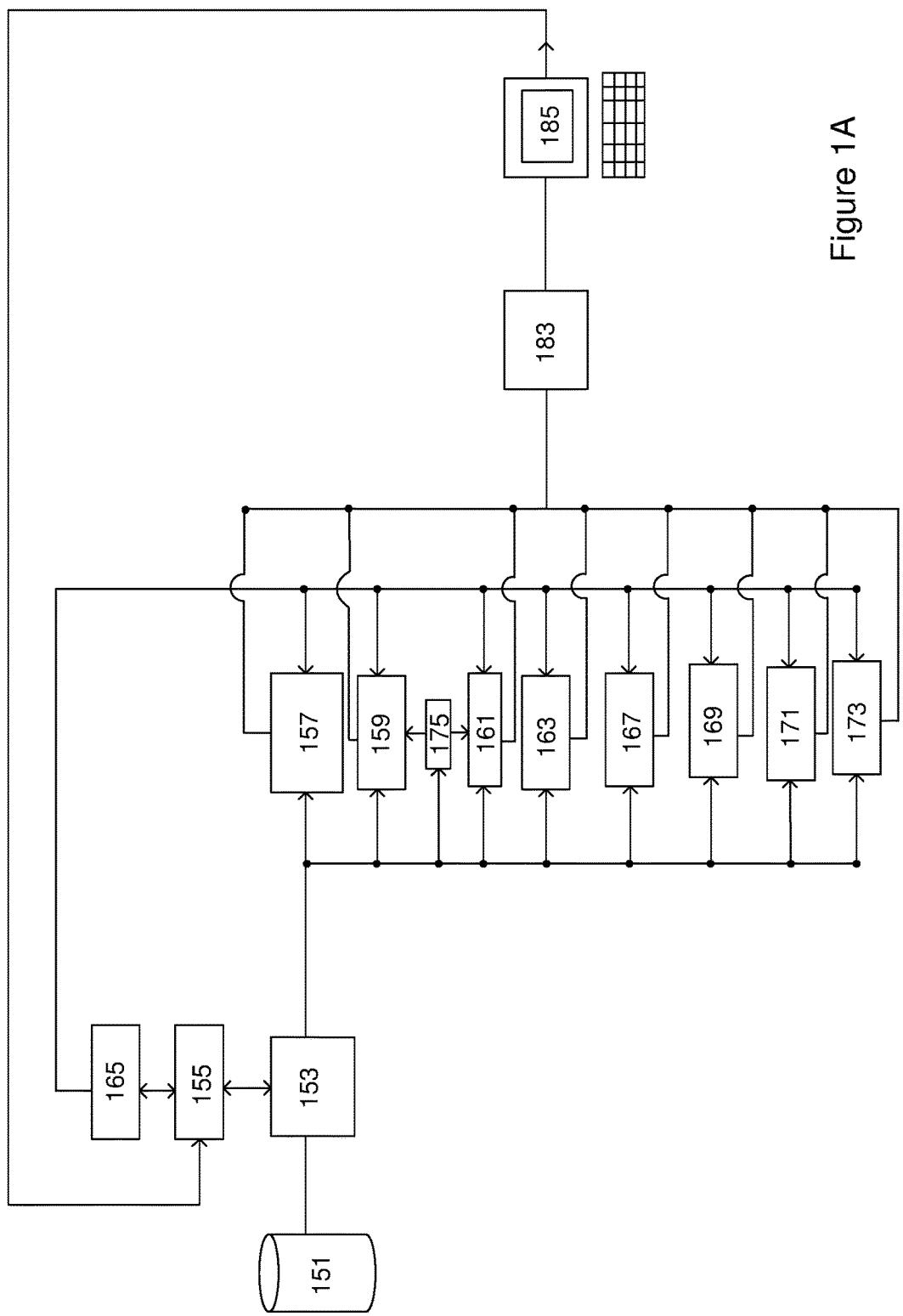
FIG. 1A shows a system block diagram of a graphical system according to an embodiment of the present invention.

The following described invention is suitable for use in conjunction with other methods, and the incorporation into one or more systems, described in an earlier filed U.S. provisional patent application by the applicant. Namely, U.S. provisional patent application 61/074,347 filed on 20 Jun. 2008, and entitled METHODS, APPARATUS AND SYSTEMS FOR DATA VISUALISATION AND RELATED APPLICATIONS, which is hereby annexed as a reference.

Embodiments of the present invention are described herein with reference to a system adapted or arranged to perform a method for representing metrics associated with a plurality of components.

In summary, the system includes at least a processor, one or more memory devices or an interface for connection to one or more memory devices, input and output interfaces for connection to external devices in order to enable the system to receive and operate upon instructions from one or more users or external systems, a data bus for internal and external communications between the various components, and a suitable power supply. Further, the system may include one or more communication devices (wired or wireless) for communicating with external and internal devices, and one or more input/output devices, such as a display, pointing device, keyboard or printing device.

The processor is arranged to perform the steps of a program stored as program instructions within the memory device. The program instructions enable the various methods of performing the invention as described herein to be performed. The program instructions may be developed or implemented using any suitable software programming language and toolkit, such as, for example, a C-based language. Further, the program instructions may be stored in any suitable manner such that they can be transferred to the memory device or read by the processor, such as, for example, being stored on a computer readable medium. The computer readable medium may be any suitable medium, such as, for example, solid state memory, magnetic tape, a compact disc (CD-ROM or CD-R/W), memory card, flash memory, optical disc, magnetic disc or any other suitable computer readable medium.

The system is arranged to be in communication with external data storage systems or devices in order to retrieve the relevant data.

It will be understood that the system herein described includes one or more elements that are arranged to perform the various functions and methods as described herein. The following portion of the description is aimed at providing the reader with an example of a conceptual view of how various modules and/or engines that make up the elements of the system may be interconnected to enable the functions to be implemented. Further, the following portion of the description explains in system related detail how the steps of the herein described method may be performed. The conceptual diagrams are provided to indicate to the reader how the various data elements are processed at different stages by the various different modules and/or engines.

It will be understood that the arrangement and construction of the modules or engines may be adapted accordingly depending on system and user requirements so that various functions may be performed by different modules or engines to those described herein, and that certain modules or engines may be combined into single modules or engines.

It will be understood that the modules and/or engines described may be implemented and provided with instructions using any suitable form of technology. For example, the modules or engines may be implemented or created using any suitable software code written in any suitable language, where the code is then compiled to produce an executable program that may be run on any suitable computing system. Alternatively, or in conjunction with the executable program, the modules or engines may be implemented using any suitable mixture of hardware, firmware and software. For example, portions of the modules may be implemented using an application specific integrated circuit (ASIC), a system-on-a-chip (SoC), field programmable gate arrays (FPGA) or any other suitable adaptable or programmable processing device.

The methods described herein may be implemented using a general purpose computing system specifically programmed to perform the described steps. Alternatively, the methods described herein may be implemented using a specific computer system such as a data visualization computer, a database query computer, a graphical analysis computer, a retail environment analysis computer, a gaming data analysis computer, a manufacturing data analysis computer, a business intelligence computer etc., where the computer has been specifically adapted to perform the described steps on specific data captured from an environment associated with a particular field.

The herein described visualization of this embodiment is used to analyze the components that make up menu items in a restaurant or café. That is, it is used to analyze the ingredients that are used to create each of the menu items or dishes listed on the menu. This example is provided to show the underlying concept of how this new visualization is produced, and it will be understood that the invention is not limited to a system that only analyzes menu items and its components but can be applied to data of many different formats and retrieved from many different systems. For example, the methods described herein may be applied to gaming data, retail data, entertainment industry data, financial data, telecommunications data, hospitality industry data, travel industry data, web analytical data, games, office based documents, products and services, merchandise, etc. Therefore, the items being analyzed using the herein described methodology should consist of a number of components, which can be grouped according to two or more grouping categories, and wherein the components and/or groups of components may be associated with a BPD (Business Performance Driver).

A Business Performance Driver (BPD) is a business metric used to quantify a business objective. For example, turnover, sales. BPDs are Facts (sometimes referred to as measures). Facts are data items that can be counted. For example, Gross Sales; Units Sold.

BPDs comprise of:
1. Measures: Data items that can be counted. For example, Gross Sales; Units Sold.
2. Dimensions: Data items that can be categorized. For example, Gender; Locations.
3. Restrictions can be applied to BPDs. These filter the data included. For example a restriction of 'State="CA"' may be specified to only include data for California.
4. Normalizations can be applied to BPDs. These specify (or alter) the time period the BPD refers to. For example—Daily Units Sold, Monthly Profit.

The combination of BPDs, Restrictions and Normalizations provides the flexibility to create many ways of looking at data without requiring extensive definition effort.

In other words a Business Performance Driver (BPD) is a 'measure' that can be normalized. Measures are data items that can be counted. For example, Gross Sales; Units Sold. BPDs might be displayed on visualizations. For example, Revenue earned per store on a map. Restrictions and/or Normalizations could be applied to a BPD. The following table provides examples of these:

| Scenario | Business Example |
| --- | --- |
| BPD (no normalization or restriction) | Revenue |
| BPD with restriction | Revenue earned in the state of California |
| BPD with normalization | Revenue earned in week 1 of 2008 |
| BPD with restriction and normalization | Revenue earned in the state of California in week 1 of 2008 |

It will be appreciated that the example provided below has been reduced in scale to enable full understanding of the concepts involved and that all data that would be expected for a real world example has been omitted for clarity purposes. It will also be understood that a greater number of linkages and elements may be implemented in a working embodiment of the invention in order to take into account all components of the items being analyzed. It will also be understood that various values and arrangements of the different elements associated with the visualization are there for explanatory purposes only and that the positioning, values or arrangement may not necessarily directly correspond with all other elements shown in the representation.

It will further be appreciated that the figures provided are in black and white for clarity purposes, but that the visualizations herein described can provide more information by using various different colors and/or shading to indicate differences between and values associated with the icons.

The visualization has several aims including enabling a user:
To understand components that form at least part of a whole, such as a menu for example where the components are the ingredients, or groups of different types of ingredient or a mixture of single ingredients and groups of ingredients.
To see the total ingredients within the menu or to understand the relationship with other ingredients.
To be able to see the various metrics (such as costs for example) associated with menu items, and the ingredients of those items.
To look at the metrics associated with the ingredients, and be able to identify metrics within, above or below certain values for certain menu items.
To be able to examine menu items and/or ingredients within a menu, and see the metric values associated with each item.
To get an overview of the number of different item groups that use different ingredient groups. To follow a cognitive analysis process from the overview to the details without changing the information presented but by putting more visual weight on that element. For example, to understand how the menu items within the menu are as a whole e.g. if the menu is more favored towards using vegetables and not costing a lot. To be able to see quickly the relative cost (or BPD) of each menu item.

The various modules of the herein described system are described with reference to FIGS. 1A, 1B and 1C.

FIG. 1A shows a system block diagram of a graphical system according to this embodiment. A data storage module 151 stores the data used by the system. A data retrieval module 153 retrieves the data for the data storage module under instructions received from various other modules in the system.

The data provided as an input to the system may be of any suitable type of data, for example, real world data including, but not limited to, gaming or gambling data associated with a gaming environment such as a casino, event data, test or quality control data obtained from a manufacturing environment, business data retrieved from an accounting system, sales data retrieved from a company database, etc. All this data may be received by the system in real time in a cache memory or may be stored in a more permanent manner. According to this embodiment, the data provided is associated with menu items provided on a menu in a restaurant or café.

The data storage module may be any suitable type of data storage system. For example, it may be an enterprise data warehouse (EDW), a data mart, a database, a storage array or any other suitable device or groups of devices that can store data for later retrieval. Further, the data storage module may be a cache memory used to temporarily store incoming data captured in real time.

A selection detection module 55 is in communication with the data retrieval module 153 to instruct the data retrieval module 153 which data needs to be retrieved from the data storage module 151.

The data retrieval module 153 is in communication with a number of icon modules (157, 159, 161, 163) which create various icons in the graphical representation.

A menu item icon module 157 creates a menu item icon. A component group icon module 159 creates a component group icon. A component icon module 161 creates a component icon. A component indicator icon module 163 creates a component indicator icon.

A highlight module 165 is used to highlight the various icons and tables upon instructions received from the selection detection module. The highlight module is in communication with the various icon modules (157, 159, 161, 163) and a number of table modules (167, 169, 171, 173).

An order determination module 175 is in communication with the component group icon module 159 and the component icon module 161 and is arranged to determine a suitable ordering of the elements of the icons.

The outputs of the various icon modules (157, 159, 161, 163), table modules (167, 169, 171, 173) are communicated to a rendering module 183, which renders the image using standard rendering techniques. The rendered image is communicated to an output module 185, such as an output display on a computer. The selection detection module 155 is in communication with the output module to enable the system to detect the selection of one of the icons or tables.

Figure 1B:
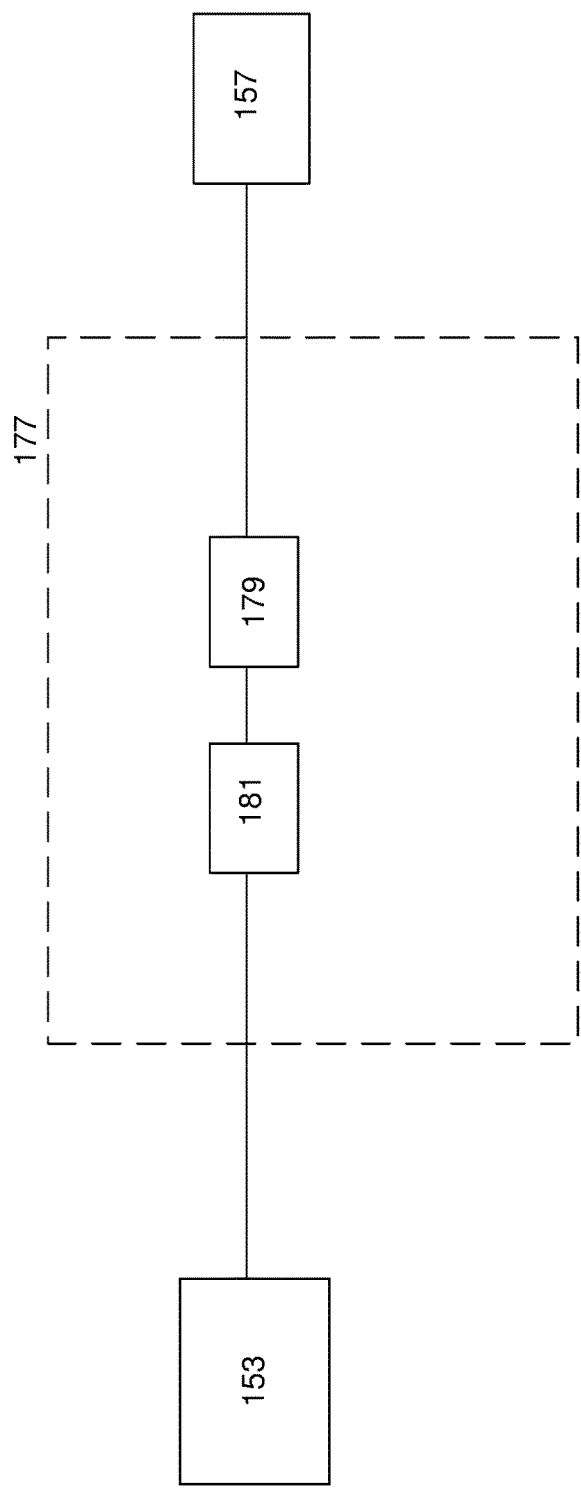
FIG. 1B shows a further system block diagram of a graphical system according to an embodiment of the present invention.

FIG. 1B shows further details of the system. A menu item placement module 177 includes an inner section module 179 and a menu item icon positioning module 181. The menu item icon positioning module 181 is in communication with the data retrieval module to receive BPD values. The menu item icon positioning module 181 is also in communication with the inner section module to limit the placement of the menu item icons. The inner section module 179 is in communication with the menu item icon module to provide instructions on where the menu item icons are to be positioned in the visualization.

Figure 1C:
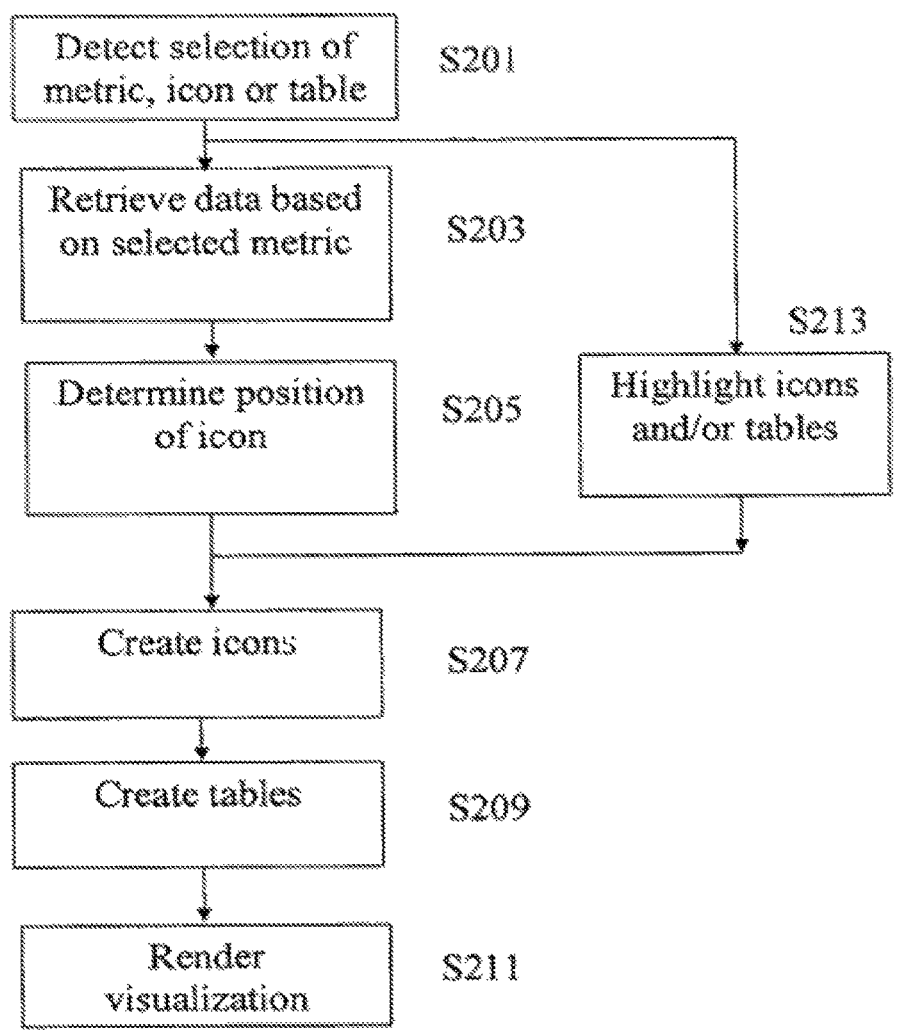
FIG. 1C shows a flow diagram of the basic methodology according to an embodiment of the present invention.

FIG. 1C shows a flow diagram of the basic methodology according to embodiments of the present invention. At step S201, the system detects a selected metric, icon or table. At step S203, the system retrieves data based on the selected metric. At step S205, the system determines the position of the icons within the visualization based on the selected metric. At step S207, the system creates the icons. At step S209, the system creates various tables. At step S211, the system renders the visualization. At step S213, the system enables highlighting of modules and/or tables that have been selected.

As an alternative to, or in conjunction with, the display module, further output modules may be provided to output the results of the rendering module. That is, the raw data retrieved by the data retrieval module is analyzed and converted to provide output data in a specific format. The output data is provided to the display and/or further output modules to enable a user to visualize the raw data in a manner that conveys more useful or hidden information that would otherwise be lost.

The further output module may be a printing device in communication with the described system to receive print control data so that representations of the data may be printed on any suitable print medium. Alternatively, the further output module may be an interface that enables the data output from the rendering module to be interfaced with other data handling modules or storage devices. As a further alternative, the output module may be the same or different data storage module as described above.

This embodiment of the invention will be described with reference to three modes of operation. The first mode described is an "Overview mode".

Figure 2A:
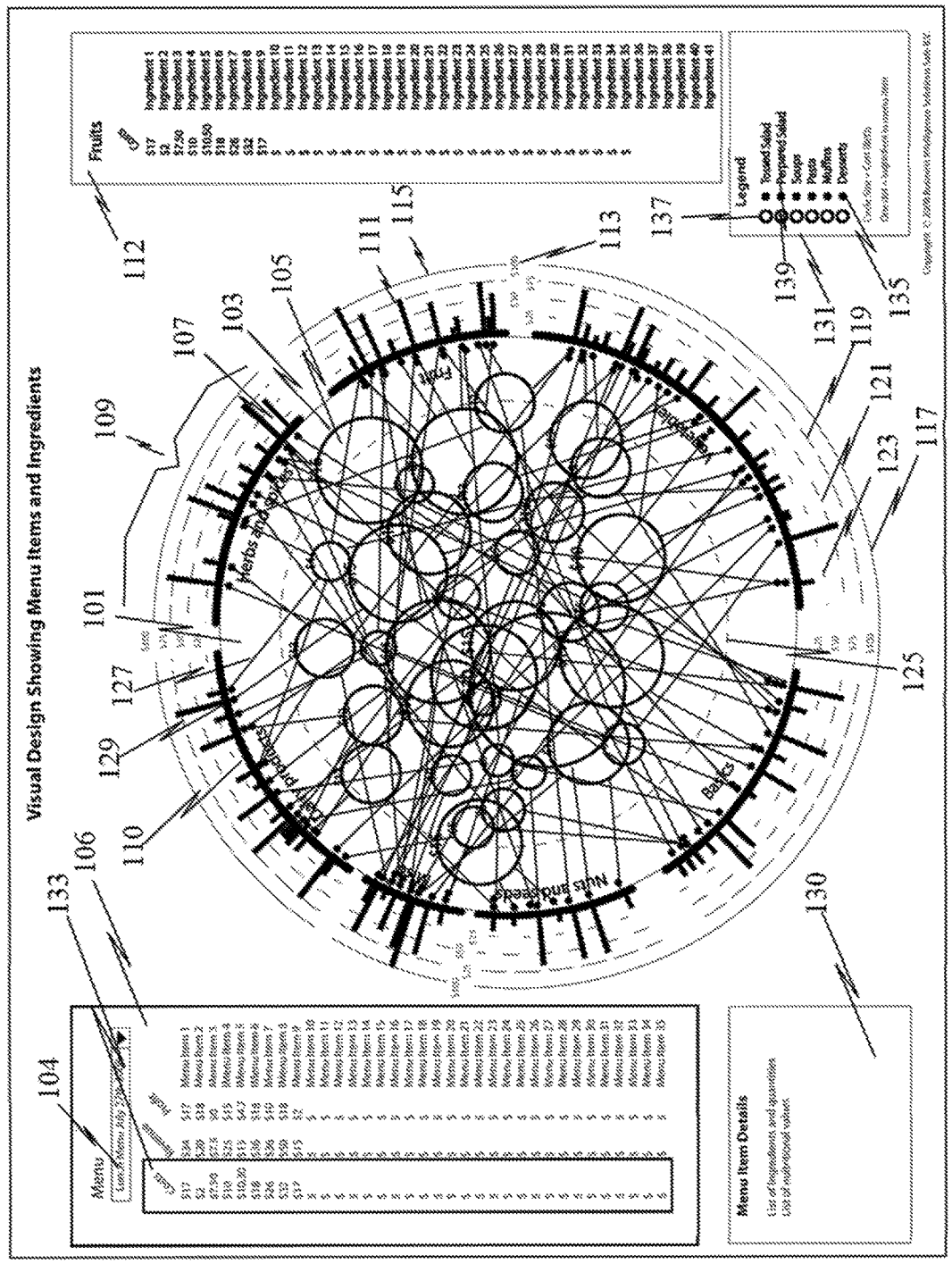
FIG. 2A shows a graphical representation of component analysis as used on menu item components according to an embodiment of the present invention.

Referring to FIG. 2A, a graphical representation according to this embodiment is provided. It will be understood that the various representations in the figures are provided in black and white for clarity purposes only, and that various color schemes, gray scales or transparencies may be used, and may be preferred, for representing the various elements of the representation.

The overview mode of display is designed to get an overview, and it allows the user to examine and explore the details of the various relationships and elements if they so wish.

There are five sections that make up this visualization, and aid the user in understanding the menu structure and elements. These are described below.

The Central Section 101 is arranged in an area in the shape of a circle, and has been designed to show a number of features. It will be understood that, as an alternative, the shape of the central section may be any other suitable graphical shape, such as geometric shape, organic shape, or dodecagon spiral.

In the central section are shown the following features:

Each menu item is represented by a menu item icon in the form of a colored circular ring 103 surrounding a circle 105. It will be understood that although the image in FIG. 2A is shown in black and white, each of the rings 103 surrounding each circle 105 may consist of various different colors as will explained in more detail below. Also, the circles 105 may be filled in with a suitable grey scale color or an alternative color, or may be left unfilled. This fill color may also have transparency.

A menu item table 106 is created by a menu item table module. This module retrieves the menu items from the data store that are associated with the selected menu. Also retrieved are the metrics (BPDs) associated with each of the menu items. The menu items are arranges in a list within the table indicating the BPD values associated with each.

The metric (BPD) associated with each menu item is selectable by a user from a menu item table 106. That is, the user may click on the graphical representation using any suitable input device, such as a mouse, touch screen etc, and the selection detection module detects the selection of the relevant metric (BPD) in the table 106. The selection detection module instructs the data retrieval module to retrieve the data associated with the selected BPD. In this example, the user may select a BPD from any one of costs, revenue and profit by selecting the appropriate column in the table 106. Selection of the metric (BPD) may also be accomplished by using standard user interface controls, for example, by using a dropdown menu or a dropdown list box. Cost has been selected in this particular example, and is indicated within the representation in two different ways.

Firstly, the metric is displayed in text format by the menu item icon module. For example, a dollar value ($16) 107 is positioned in the top portion of each menu item icon. In this particular example, the text is positioned at the top of the icon.

Further, the metric value is used by the menu item icon module to calculate the diameter of each menu item icon. That is, the diameter of each menu item icon is based on the metric value associated with each menu item each icon is representing.

The color of the circular ring of the menu item icon is based on data retrieved by the data retrieval module, where that retrieved data is associated with the menu item. That is, the categories in which each of the menu items can be placed is used by the menu item icon module to create the menu item icon using the associated colors for the menu item categories. For example, in this embodiment, each menu item may be classed as a particular type of meal, such as a tossed salad, prepared salad, soup, pasta, muffin or dessert. Therefore six different colored rings are provided in this example to identify the six different meal categories.

It will be understood that the color of the menu item icon may be used to represent other metrics. For example, the color may represent discrete value categories (e.g. low, medium and high sell items or the age of the menu item: 1 day, 3 days, 5 days, 10 days and 20 days for example), or continuous metrics such as the weight of items.

Therefore, for each menu item or whole menu, a graphical indication is provided in the form of one or more icons, the icon(s) is represented based on the selected metric. Additional information is also provided in the form of further icons to represent additional group information associated with the components that form the menu items.

Around the outer edge of the central section 101 are arranged the individual components (e.g. ingredients) that make up the menu items. The components are grouped together according to a defined category. In this example, the ingredients are grouped according to the food group 109 in which the ingredient belongs. For example, the ingredient may be grouped in the category dairy products, herbs and spices, fruit, vegetables, basics, nuts and seeds or and miscellaneous. Each ingredient will fall within a single one of these food groups.

Each food group (component group) is represented by a component group icon module which is used to create a component group icon 110, which, in this embodiment is a partial arc positioned around the periphery of the central section.

As explained in more detail below, each ingredient is represented using a component icon in the form of a bar that extends radially outwards from the component group icon (partial arc icon 110). Only one bar is used to represent each ingredient. On the internal side of the component group icon 110, each ingredient is identified as being used in one or more menu items by the use of a component indicator icon. Each component indicator icon links to a single menu item icon. The number of component indicator icons for each ingredient represents the number of menu items in which the ingredients are used. Each component indicator icon is colored according to a menu item category (meal type) in which the menu item belongs. Therefore, for each single ingredient, there may be one or more component indicator icons (depending on the number of menu items that use the ingredient). If there are multiple component indicator icons for a single ingredient (because it is used in multiple menu items), these may be represented using the same or different colors depending on the menu item category in which the menu items belong.

The component group icons are user selectable. The selection detection module detects when a user selects the icon using any suitable computer input device, such as a pointing device. Upon selection the selection detection module instructs the highlight module to highlight the icon. As an alternative, selection may be carried out using another implementation such as dropdown menus and list boxes, not shown here.

The detected selection also causes the selection detection module to instruct the data retrieval module to retrieve the list of components (ingredients) within that group. The component group table module updates the component group table 112 (top right of display) so that the ingredients within the selected group are displayed along with the BPD values of the BPD category selected by the user and retrieved by the data retrieval module. The user is thus able to interact with the visualization to change and visualize a selected ingredient group by selecting any other component group icon for the other ingredient groups. The selected group is highlighted using the highlight module. For example, the icon for the selected component group may be represented by a different or enhanced arc color. Further, the highlight module may represent the individual ingredient bars by a different or enhanced bar color.

The order in which each component is positioned within each of the groups (e.g. food groups), and the order in which each of the groups (e.g. food groups) is positioned around the periphery of the graphical representation is determined by an order determination module. The order determination module uses any suitable heuristic algorithm, such as those associated with the traveling salesman problem. That is, an algorithm is implemented by the order determination module on the data associated with the components so that a reasonable solution is provided. A reasonable solution means that the maximum correlation (or minimum statistical distance) is obtained between each of the components (e.g. ingredients) or the component groups (e.g. food groups). Alternatively, the menu items may be arranged using metrics and dimensions relating to other aspects of the business, such as revenue or the number of days items have been on the menu, for example.

For example, the order determination module may use nutritional values to determine the statistical distance between two components within the same component group. It will be understood that other factors may be used to determine statistical distance, such as: component cost (or other monetary value); component type, size, weight (or other physical measurement); component build details (e.g. whereabouts the component is listed in a bill of materials); component value, etc.

By applying the same statistical distance calculations to all the components in the group a best fit order of components is produced so that components having maximum correlation with other components are placed closer together than those that have less correlation.

The component icon module represents each component (e.g. ingredient) around the outer edge of the central section by creating an icon 111 in the form of a bar. It will be understood that, as an alternative, the individual components (e.g. ingredients) may be represented using any other suitable form of icon. For example, the icon may be in the form of any or a combination of text matter, numbers, letters, characters, lines, geometric shapes, organic shapes, images or objects.

The icon for the ingredient (component icon) is graphically represented based on the total value of the selected metric (e.g. cost) associated with the component. That is, the size of the bar 111 in this example is automatically graphically represented using the component icon module based on the total cost value for the ingredient in all of the menu items. It will be understood that, as an alternative, the total value of the metric selected by the user may determine at least one of the shape, shading, color, height, or size of the icon for the ingredient. Depending on which metric is selected by the user, the icon will change accordingly based on the metric value.

Calibration values for overall cost of an individual ingredient are also provided in the graphical representation by the component icon module using text 113 and concentric circles 115, where the line-style of the circles gives a visual indication of the scale.

That is, in this example, four concentric circles are created by the component icon module, the outer most circle 117 has a solid line indicating that its value is full scale (in the example above this is $100), the next line 119 is made up of lines and spaces, with 75% line and 25% space, indicating 75% value ($75). The same visual coding is used for the last two lines (121 and 123) where 25% line=$25 and 50%=$50. This coding will be used for any BPD displayed/selected, having the full scale dollar value (or whatever unit the BPD is represented in) being equal to the 100% line circle.

A further icon in the form of a component (ingredient) indicator icon may be provided by a component indicator icon module around the circumference of the central section to indicate which of a number of particular components (ingredients) are used in a menu item, in which menu group the menu item belongs and also in which food group the ingredient belongs when used in that menu item.

In this example, the ingredients are first grouped according to the type of meal the menu item using the ingredient is associated with. For example, the ingredients used in a menu item such as a chocolate cake would be placed in the grouping for desserts. Other groupings include tossed salads, prepared salads, soups, pastas, muffins as well as desserts.

Further, each ingredient falls within a further group type based on the food group in which the ingredient is categorized. For example, cream used in the chocolate cake menu item would be categorized as a dairy product and as such the cream (when used in the chocolate cake) falls in the categories dairy products and desserts.

It will be understood that other alternative groupings for the components may be used.

In this embodiment, the component indicator icon is a dot and is used, amongst other things, to indicate that the ingredient has been used in a particular menu item. The color of the dot indicates the ingredient is categorized within a particular group (other than belonging to that menu item). For example, the category may be the type of meal to which the menu item belongs i.e. Salad, Soup, Muffin etc. There is a separate icon for each ingredient in each menu item. These icons are also referred to as ingredient element dots.

Further, the placement or positioning of the component indicator icon is arranged according to a grouping different to that of the menu item meal type group. That is, the component indicator icon is positioned inside the arc representing the component group (component group icon) in line with the component icon (bar 111) that represents that ingredient.

The user is able to dynamically interact with the BPD as explained above by selecting another BPD to be displayed, through the selection of the required BPD column in the menu item table 106 (top left hand box). That is, the selection detection module detects the selection of a column (BPD) in the table 106 and instructs the data retrieval module to retrieve the values associated with the selected metric. These metric values are then made available to the other modules in the system.

The user is also able to dynamically interact with an inner section as represented by an inner circle (Menu Item Circle Size Controller) which is indicated by the dashed line 125 within the central section 101. A menu item placement module includes an inner section module that enables a user to change the radius of the inner section (i.e. the inner circle size). The inner section defines an inner area of the central section in which each of the menu items is to be represented. This is done by the inner section module detecting the user, using any suitable input device, changing the position of the dashed line that represents the outer circumference of the inner section. For example, the radius of size or area of the inner section may be changed by a user selecting a point on the circumference of the inner section and sliding the point inwards or outwards to change the circumference. Alternatively, specific values may be entered by the user for a suitable circumference, radius or diameter of the inner section. Further, the inner section size may be adjusted automatically as explained below.

The outer circumference of the inner section represents a maximum circumference of an area located around the central point of the central section. This area is where the central points of the menu item icons can be positioned without the menu item icon interfering with other elements of the representation and without the icon extending beyond the central section. For example, it may be undesirable to have the menu item icons being positioned over the ingredient indicator icons so that they are obscured from view.

Therefore, the calculated radius of the central section minus the selected, detected or calculated radius of the inner section represents the maximum radius of the largest menu item circle(s).

In equation form, this is represented by:

$$A <= B - C$$

where A=Radius of largest menu item icon; B=Radius of main circle (central section); C=Radius of inner circle (inner section).

It will be understood that the menu item icon radius is likely to change upon selecting a new metric (BPD), and so the system automatically adjusts the radius of the inner section in order to keep all the menu item icons within the central section without overlapping other areas of the representation. That is, the menu item icon positioning module in conjunction with the inner section module determines the maximum radius of the menu items (based on the selected BPD) and adjusts the inner section radius accordingly based on the above equation.

For each of the icons (circles 105 and rings 103) representing the menu item, the menu item icon module graphically represents an interconnecting line 127 from the menu item circle 103 to the component indicator icon (ingredient dot) 129. There is one interconnecting line for each ingredient (component) within the menu item between the component indicator icon and the menu item icon. In the overview mode the lines preferably have a low visual presence and so are displayed in a light gray scale or with a level of transparency.

The positioning of the menu item icons 103 within the central section is based on a number of factors. These factors include the components (e.g. the ingredients) that make up the menu item and the relative metric (BPD) values (as selected by the user) for each of those components. The position of the icons 103 is calculated by the menu item icon positioning module based on a spring force system (with constraining outer limits) and will be discussed in more detail below.

It will be understood that transparency of the menu item icons, ingredient lines (going from the menu item icons to the component indicator icons) and component indicator icons (ingredient element dots), may be adjusted by the various icon modules described herein to allow overlapping and the ability to see the whole picture.

Figure 3:
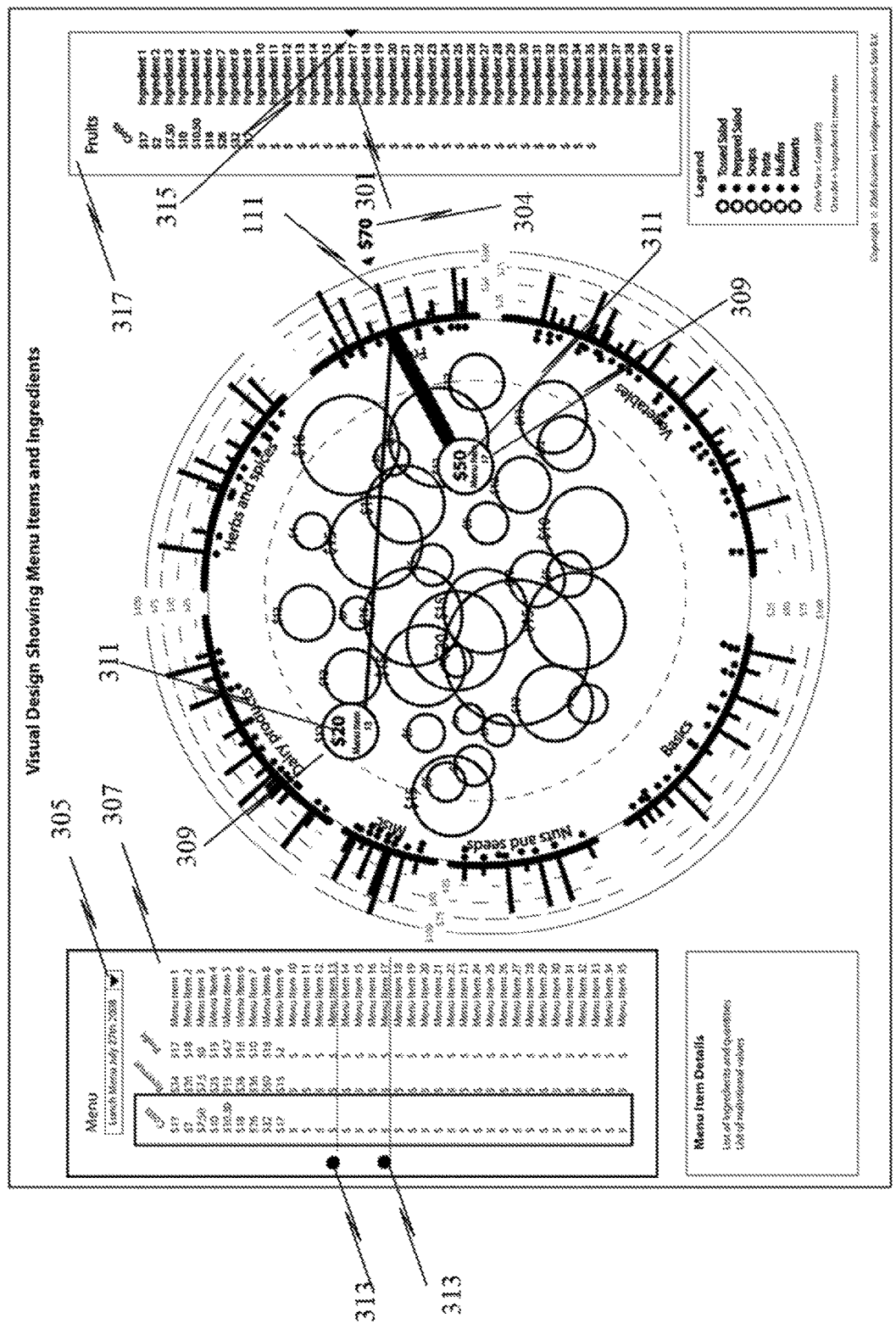
FIG. 3 shows yet a further graphical representation of component analysis according to an embodiment of the present invention.
Figure 4C:
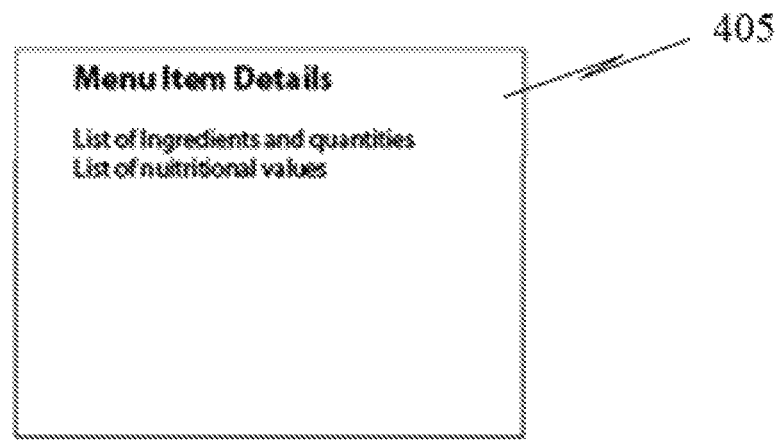
FIG. 4C shows a detailed view of a further information menu shown in the graphical representations of FIGS. 1, 2 and 3.
Figure 4D:
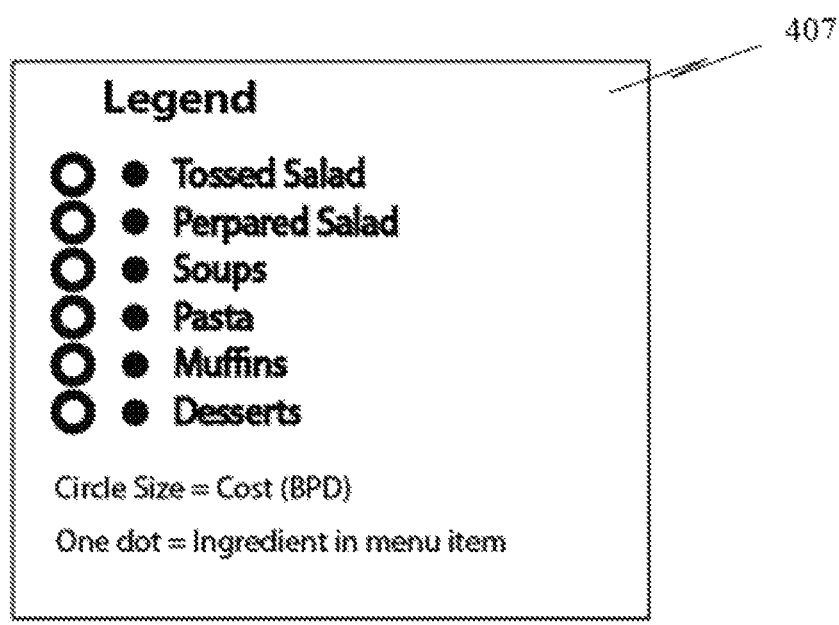
FIG. 4D shows a detailed view of a legend shown in the graphical representations of FIGS. 1, 2 and 3.

Details of the various elements described are shown in FIGS. 4A to 4D and 5 to 10, where FIGS. 4A and 4B show detailed views of the menu items 106 and 112, FIG. 4C shows a detailed view of a further information menu 130 and FIG. 4D shows a detailed view of a legend 131 indicating the menu item food types. FIGS. 5 to 10 show detailed views of portions of the graphical representation of FIGS. 1, 2 and 3.

A second section of the visualization, a menu item table 106, includes the following elements and interaction capabilities.

A dropdown list 104 is provided that allows the user to select different menus for display. In this example, the menu selected is a lunch menu for Jul. 27, 2008. Upon selection, data associated with the selected menu is retrieved or at least identified for later retrieval. The data associated with the selected menu may include the menu items in that menu, the ingredients within each menu item, BPD values associated with each of the menu items, BPD values associated with each of the ingredients, grouping (category) information for the menu items, grouping (category) information for the ingredients Different BPDs associated with the menu being displayed can be selected as discussed above by selecting the appropriate column in the displayed menu item table 106. In the accompanying figures only one of the BPDs is visualized in the central section of the visualization using the methodologies herein described. However, it will be understood that, as an alternative, multiple BPDs may be visualized together in the central section.

In the example herein described, the menu item table module displays Costs, Revenue and Profit in the menu item table 106. The metric "Costs" has been selected by the user and the metric is visualized in the central section in relation to each of the menu items in the selected menu. The selection of this BPD is indicated by the highlight module highlighting the column 133 in the menu item table 106 by generating a box around the BPD values. The selection of the BPD may be highlighted by the icon highlighting module using other suitable methods. For example, the highlight may be realized by applying any suitable or different form or color to the column.

The user is able to select a different column (e.g. Revenue or Profit) to visualize different BPDs using any suitable input device, such as a pointing device (e.g. a computer mouse).

The user is able to select different Menu Items in the list by clicking the particular Menu item of choice, e.g. Menu Item 1, Menu Item 2 etc. It will be understood that the different menu items are preferably named according to the item in order to enable the user to more easily understand its relevance. For example, the menu items may be the name of a particular dish available at a restaurant. Further, the menu items may be grouped. For example, the menu items may be grouped according to starters, main course and desserts. The selection of the BPD results in the system retrieving and displaying the BPD details of the ingredients that are used within all of the menu items listed; see "Menu Item Ingredient Mode" below.

When the system detects that the user is using the input device to hover a cursor (or the like) over a particular menu item within the menu list 106, additional details associated with that menu item may be retrieved from the data store and the menu item table module may display the additional information in a window overlaying the visualization. The type of additional information may be user defined or system defined. It could be, for example, nutritional data associated with the menu item.

A third section of the visualization, the "Ingredient Group Details" menu 112 (component group menu), shows the details of the ingredient group associated with the ingredient group icon (component group) as selected by the user. For example, the user may select the "fruit" grouping for ingredients by selecting the arc representing the fruit ingredients placed around the circumference of the outer section. The component group table 112 is created by the component group table module, which uses the data retrieved by the data retrieval module to list all the ingredients that fall within the category of a fruit.

Further, the component group table module uses the retrieved BPD values for each of the components (ingredients) to displays the sum for the selected BPD (for example, Costs) for each of the ingredients within the table 112. The values displayed here may be changed by user interaction. That is, the user may select another ingredient group (e.g. dairy products, herbs & spices), or a different BPD (e.g. revenue or profit), and these selections will change the ingredients (components) listed in the table 112, and also display the selected BPD values for the components of the selected component grouping.

Interaction with the component group table 112 provides the user with the ability to select a particular ingredient (component) from the list in the table 112 and see where the costs (or other selected BPD) come from. This is explained in more detail below in the "Ingredient Breakdown Mode" below.

There is a one to one link between the component icons (bars) 111 indicating the individual ingredients and the ingredient items listed in the table 112. It will be understood that zero values in the table 112 are represented by the absence of a bar.

A fourth section of the visualization, the menu group legend 131, is created using a menu group table module. This menu group legend displays further details that assist in the understanding of the visualization. In this embodiment, the further details are the menu groups in which each of the menu items, and associated ingredients, belong. It includes the following interactions.

The menu group table module creates an interactive legend listing the different menu groups in which menu items can belong. Next to each definition in the list is provided a representation of a component indicator icon using a color assigned to that menu group. Also next to each listing is provided a representation of a ring of a menu item icon using a color assigned to that menu group. Each listing in the legend 131 is provided with a unique color assignment to enable a user to easily see in which menu group each of the menu items below, and also to see in which menu group each ingredient belongs (for specific menu items).

The selection detection module detects when a user selects a dot 135 (representing a component indicator icon) within the menu group legend 131, and is arranged to highlight all the dots that are associated with the same menu item group on the visualization (around the inner edge of the outer circle). Each dot represents an ingredient belonging to a different menu item group (soups, pasta etc) and is indicated in a different color. Therefore, dots representing different ingredients within the same menu item group will be represented by the same color. For example, any ingredient used in a soup will be represented using the color assigned to the soup grouping. Any ingredient used in a salad will be represented using the color assigned to the salad grouping. Although the same ingredient may be used more than once, for example in different menu items, a separate record of that ingredient is stored for each separate use. For example, tomatoes used in a soup may be represented using a first color (e.g. a blue dot), whereas tomatoes used in a salad may be represented using a second color (e.g. a red dot). Therefore, for a particular ingredient, there may be one, two or more different colored component indicator icons placed in the visualization to show that the ingredient has been used in one, two or more different menu item groups. Each of the separate component indicator icons will be linked to a separate menu item icon in a one to one relationship.

As an example, if the user of the system wishes to highlight all the ingredient elements for Tossed Salad, then they select the dot for Tossed Salad shown in the legend 131.

This results in the selection detection module determining which dot is selected and which group that selected dot represents. Subsequently, all component indicator icons in the representation that fall within that grouping are highlighted by the highlight module. Although the dots are already colored appropriately to show the different menu item groups, selection will make this visual importance much greater and hence ensure that the dots associated with the selection stand out from the other dots. For example, the highlight module brightens the dots that fall within the selected category and darkens all other dots. Also, the colors of the selected dots may be enhanced while the other dots may be made black and white.

If the user selects a circle 137 within the legend 131, the selection detection module detects this and instructs the highlight module to highlight the associated menu item icons 103 for that particular menu item group (i.e. menu item type) in a similar manner as described above.

If the user selects the text 139 indicating the menu group within the legend 131, the selection detection module detects this and instructs the highlight module to highlight both the component indicator icons and the menu item icons that fall within that menu item group (i.e. menu item type).

Figure 2B:
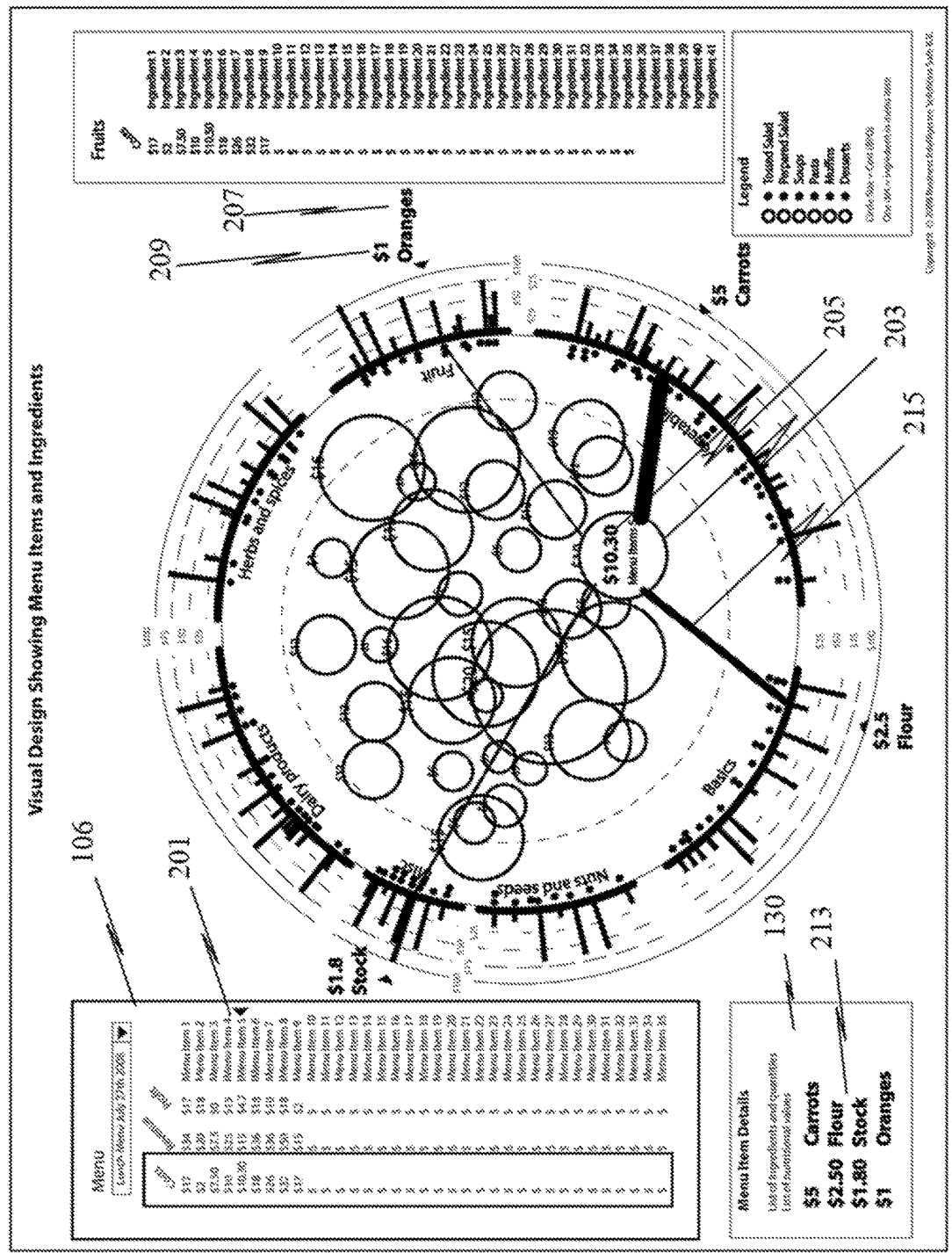
FIG. 2B shows a further graphical representation of component analysis according to an embodiment of the present invention.

Referring to FIG. 2B, a second mode of operation is now described.

This mode of visual display is designed to look at an individual menu item, and the ingredients (components) that make up that menu item. To access this mode the user can either select an individual menu item 201 from the top left menu item table 106, or select a menu item icon 203 displayed within the central section of the visualization.

When the selection detection module has detected the user has selected one of the menu items listed in the menu 106 or a menu item icon 203 the following elements are visualized within the graphical representation by identifying and retrieving the associated data.

That is, the selection detection module instructs the data retrieval module to retrieve the data associated with the selected menu item and instructs the component group table module to list the ingredients within the menu item, and instructs the menu item icon module to display the associated selected BPD value (e.g. cost) and the ingredient group(s) that they belong to.

Also indicated in the graphical representation is the relative proportion of each of the menu ingredients within the selected menu item. In this embodiment, this is shown in the manner described below, but it will be understood that the relationship between the selected menu item and the associated groups, ingredients and BPDs may be displayed using any or a combination of these visualizations.

The total Cost (or other selected BPD) values are indicated by the menu item icon module in text format 205, e.g. $10.30, within the menu item icon 203. The component icon module lists the ingredient names 207 around the edge of the outer section along with the values for each ingredient 209.

Also, in a fifth section of the visualization, a Menu Item Detail panel 130, the ingredients and associated BPD values are listed 213. This menu item details box is created by a menu item details table module. This module instructs the data retrieval module to obtain the details of the selected or relevant ingredients and displays the retrieved data in the menu item details box.

Interconnecting lines 215 between the menu item circle and each of the ingredients making up that menu item are graphically represented by the menu item icon module. The width of the interconnecting lines going from the component indicator icon to the menu item icon is varied by the menu item icon module based on the BPD data retrieved by the data retrieval module to indicate the relative proportion of the ingredient items for the selected BPD.

A menu item placement module includes a menu item icon positioning module that calculates a position to place the menu item icon within the central section of the representation. The position is based on the relative proportion of the associated ingredient items for the selected BPD. The positioning provides an overall indication of the relative proportions of the different ingredients in a visual manner to enable the user to easily interpret the relative importance of the components that make up the menu item (for the selected BPD).

Effectively, the menu item icon positioning module (in conjunction with the inner section module if used) calculates the position of the menu item icon by assuming each ingredient position (around the edge of the central section) creates a pulling force on the menu item circle icon. The larger the cost (or other BPD) for each of the ingredients the larger the pull on the menu item circle. As a formula, the force applied by each ingredient will be calculated as:

$$\text{Force} = \text{cost (or other BPD)} * \text{distance to ingredient.}$$

The distance to the ingredient is the distance from the periphery of the central section to the menu item icon centre (circle 105). That is, the central section periphery will be located at a fixed distance from the centre of the central section and positioned around the circumference of the central section.

The sum of the forces must be zero (or at least constrained to the inner section defined by the dashed circle 125 and have a local minimum). The algorithm used in this embodiment by the menu item positioning module is described in more detail below.

The basic equation to solve is that the Sum of All forces=0. That is, a state of equilibrium is reached based on the effective pulling forces of each of the ingredients based on their associated selected BPD values.

Each ingredient effectively applies a force, where force=cost (or any BPD in question) multiplied by the distance to the menu item icon center from the component indicator icon (ingredient dot).

The Sum of forces is broken down into the x and y axis components of the visualization to find the solutions so that Sum of force$_x$=0 and Sum of force$_y$=0.

Figure 11:
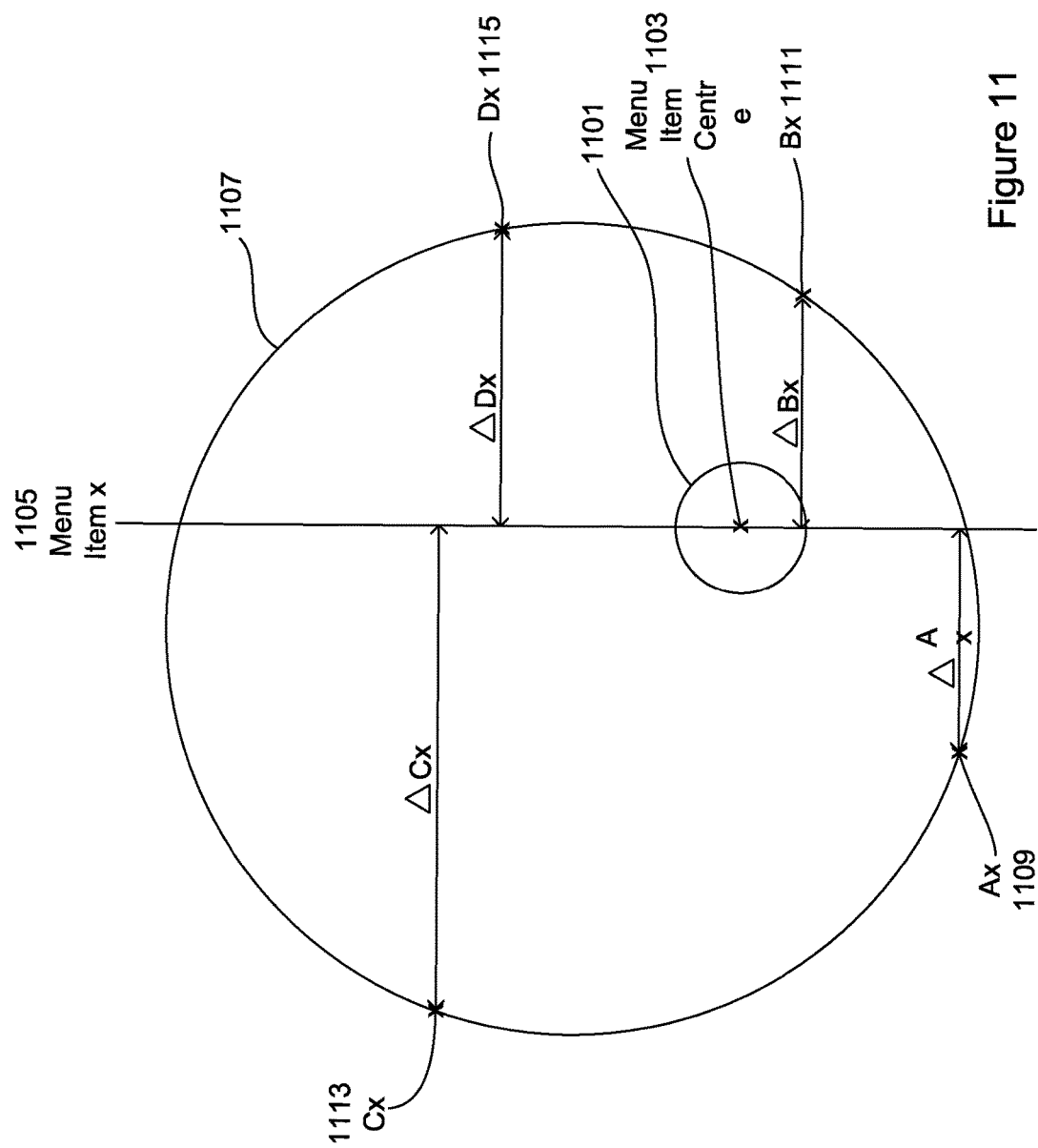
FIG. 11 shows a positioning calculation method according to an embodiment of the present invention.

Relating this to the menu item icon 203 and the force applied by the four ingredients as shown in FIG. 2B and represented in FIG. 11, the X value 1105 for the centre point 1103 of the menu item icon 1101 is calculated by the menu item icon positioning module first.

Around the periphery 1107 of the central section are located the four ingredients (A, B, C and D) that make up the menu item associated with the menu item circle 1101. That is, for the x-axis, ingredient A is positioned at point Ax 1109, ingredient B is positioned at point Bx 1111, ingredient C is positioned at point Cx 1113, ingredient D is positioned at point Dx 1115.

Value ΔAx represents the difference on the x-axis between the menu item circle centre point x position and Ax. The same applies for the relevant positions Bx, Cx and Dx, for values ΔBx, ΔCx and ΔDx respectively.

The equation is thus the combination of all forces=0. The force applied by each component (ingredient) is the BPD value associated with that component (e.g. cost) multiplied by the Δ value for that component (ΔAx etc.).

Alternatively, the menu item icon positioning module may use other factors such as applying a power factor of 2 (or more) to the ΔAx value.
Therefore:

$$(\Delta A_x * \text{Cost } A) + (\Delta B_x * \text{Cost } B) + (\Delta C_x * \text{Cost } C) + (\Delta D_x * \text{Cost } D) = 0$$

It is known that:

$$\Delta A_x = \text{Menu Item } X - Ax,$$

$$\Delta B_x = \text{Menu Item } X - Bx$$

$$\Delta C_x = \text{Menu Item } X - Cx$$

$$\Delta D_x = \text{Menu Item } X - Dx$$

where Menu Item X=x co-ordinate of the menu item icon. These values are substituted into the equation to give:

$$[(\text{Menu Item } X - Ax) * \text{Cost } A] + [(\text{Menu Item } X - Bx) * \text{Cost } B] + [(\text{Menu Item } X - Cx) * \text{Cost } C] + [(\text{Menu Item } X - Dx) * \text{Cost } D] = 0$$

By multiplying out the Cost values, the following equation is produced:

$$[\text{Menu Item } X * \text{Cost } A] - [Ax * \text{Cost } A] + [\text{Menu Item } X * \text{Cost } B] - [Bx * \text{Cost } B] + [\text{Menu Item } X * \text{Cost } C] - [Cx * \text{Cost } C] + [\text{Menu Item } X * \text{Cost } D] - [Dx * \text{Cost } D] = 0$$

Rearranging this by taking out the common factor Menu Item X, the equation becomes:

$$\text{Menu Item } X * (\text{Cost } A + \text{Cost } B + \text{Cost } C + \text{Cost } D) - [Ax * \text{Cost } A] - [Bx * \text{Cost } B] - [Cx * \text{Cost } C] - [Dx * \text{Cost } D] = 0$$

Rearranging the above produces:

$$\text{Menu Item } X * (\text{Cost } A + \text{Cost } B + \text{Cost } C + \text{Cost } D) = [Ax * \text{Cost } A] + [Bx * \text{Cost } B] + [Cx * \text{Cost } C] + [Dx * \text{Cost } D]$$

Rearranging the above produces:

$$\text{Menu Item } X = ([Ax * \text{Cost } A] + [Bx * \text{Cost } B] + [Cx * \text{Cost } C] + [Dx * \text{Cost } D]) / (\text{Cost } A + \text{Cost } B + \text{Cost } C + \text{Cost } D)$$

Values for Costs as retrieved by the data retrieval module are substituted in by the menu item icon positioning module, where Cost A=$2.50, Cost B=$5.00, Cost C=$1.80 and Cost D=$1.00. Further, ingredient x-axis positions are substituted in to produce:

$$\text{Menu Item } X = ([250 * 2.5] + [644 * 5] + [18 * 1.8] + [684 * 1]) / (2.5 + 5 + 1.8 + 1)$$

Although actual cost values are used in this calculation it will be understood that, as an alternative, percentage values may also be used.

Therefore, the menu item icon positioning module calculates the x position of the menu item icon to be 442.85.

Solving for the Y-axis position in a similar manner produces:

$$\text{Menu Item } Y = ([Ay * \text{Cost } A] + [By * \text{Cost } B] + [Cy * \text{Cost } C] + [Dy * \text{Cost } D]) / (\text{Cost } A + \text{Cost } B + \text{Cost } C + \text{Cost } D)$$

where Menu Item Y=y co-ordinates of menu item icon.

The menu item icon positioning module retrieves and substitutes values for Costs and ingredient y-axis positions to produce:

$$\text{Menu item } Y = ([12 * 2.5] + [160 * 5] + [456 * 1.8] + [422 * 1]) / 10.30$$

Therefore, the menu item icon positioning module calculates the y position of the menu item icon to be 201.24.

In summary, to find the Menu Item X and Y positions the menu item icon positioning module calculates:

$$\text{Menu Item } Y = ([Ay * \text{Cost } A] + [By * \text{Cost } B] + [Cy * \text{Cost } C] + [Dy * \text{Cost } D]) / (\text{Cost } A + \text{Cost } B + \text{Cost } C + \text{Cost } D), \text{ and}$$

$$\text{Menu Item } X = ([Ax * \text{Cost } A] + [Bx * \text{Cost } B] + [Cx * \text{Cost } C] + [Dx * \text{Cost } D]) / (\text{Cost } A + \text{Cost } B + \text{Cost } C + \text{Cost } D)$$

Or in a general sense for any number of ingredient items:

$$\text{Menu Item}_x = \text{sum of all (Distance to Ingredient Item}_x * \text{BPD of ingredient Item)} / \text{sum of all BPDs for ingredients}$$

$$\text{Menu Item}_y = \text{sum of all (Distance to Ingredient Item}_y * \text{BPD of ingredient Item)} / \text{sum of all BPDs for ingredients}$$

Optionally, the centre of the menu item icon may be constrained to be within the Menu Item Circle Size Controller (inner section as shown by the dashed circle 125) using a suitable algorithm as explained below.

The example described above will work in most cases. However, the menu item icon may optionally be constrained by the inner section module to be within the inner section 125. Effectively this means that if the initial calculation using the equations above has a solution where the menu item icon center is calculated to be outside the inner section then the menu item icon must be constrained to be on the outer circumference of the inner section (i.e. on the dashed line 125).

Therefore, if the center of the inner section is regarded as 0, 0 then the following constraint is applied:

$$\text{Menu Item } X^2 + \text{Menu Item } Y^2 = (\text{Radius of inner section})^2$$

where Menu Item X=x co-ordinate of menu item icon, and Menu Item Y=y co-ordinate of menu item icon.

Alternatively, if we have some arbitrary center position (other than 0,0) then:

$$(\text{Menu Item } X - \text{Inner Section Centre } X)^2 + (\text{Menu Item } Y - \text{Inner Section Centre } Y)^2 = (\text{Radius of inner section})^2$$

where Inner Section Centre X=x co-ordinate for the centre of the inner section, and
Inner Section Centre Y=y co-ordinate for the centre of the inner section.

In order to calculate the icon position, the menu item icon positioning module uses the inner section module to apply the following rules:

1. The sum of the forces must be a local minimum. For example, using the four ingredients as above ([distance from A to Menu Item Center*Cost A]+[distance from B to Menu Item Center*Cost B]+[distance from C to Menu Item Center*Cost C]+[distance from D to Menu Item Center*Cost D]=local minimum), or in a general sense: sum of all (distances to menu item icons*BPD of menu item)/sum of all BPDs=local minimum. and
2. (Menu Item X−Inner Section Centre X)²+(Menu Item Y−Inner Section Centre Y)²=(Radius of Inner Section)²

Alternatively, a solution may be found by stepping around the outer circumference of the inner section to find a local minimum.

Referring to FIG. 3, a third mode, the "Ingredient Breakdown Mode" is described. This mode helps the user review the ingredient cost per menu, and how this relates to the menu items.

To access this mode, the user can either click (select) the ingredient item 301 in the component group table 317 (the top right menu 112 in FIG. 2A, or as shown in FIG. 4B) or click (select) the ingredient element 111 (component icon) in the central visualization; i.e. the radial bar projecting outwards on the periphery of the central section.

When the selection detection module has detected that one of the ingredient items 301 in the table 112 or component icons 111 has been selected, one or more of the following actions are performed in the graphical representation.

The total cost 304 for the selected ingredient for the menu is retrieved by the data retrieval module and displayed by the component icon module. That is, the system displays the total cost (or other selected BPD) for the selected ingredient for the menu that is selected from the menu item table 307 (the left upper menu) from the drop down list 305.

The highlight module highlights the menu item icons 309 associated with the menu items that use the selected ingredient.

The absolute cost 311 (or other selected BPD) of the selected ingredient for each highlighted menu item is retrieved by the data retrieval module and displayed by the menu item icon module. For example $20 is indicated for menu item 13 and $50 is indicated for menu item 17.

In addition, the menu items in the menu selected from the drop down list 305 that include the selected ingredient are highlighted by the highlight module by applying a highlight icon 313 to the menu item table.

Also, the ingredient selected is highlighted by the highlight module by applying a highlight icon 315 to the ingredient list 317.

FIG. 4A shows a more detailed view of the menu item list 106.

FIG. 4B shows a more detailed view of the ingredient list 112.

FIG. 4C shows a more detailed view of a menu item details box 130 where details of the selected or relevant ingredients and quantities may be retrieved and displayed. Further information associated with the selected elements, for example in the form of nutritional information, may also be displayed here.

FIG. 4D shows a more detailed view of the legend box 131.

Figure 5:
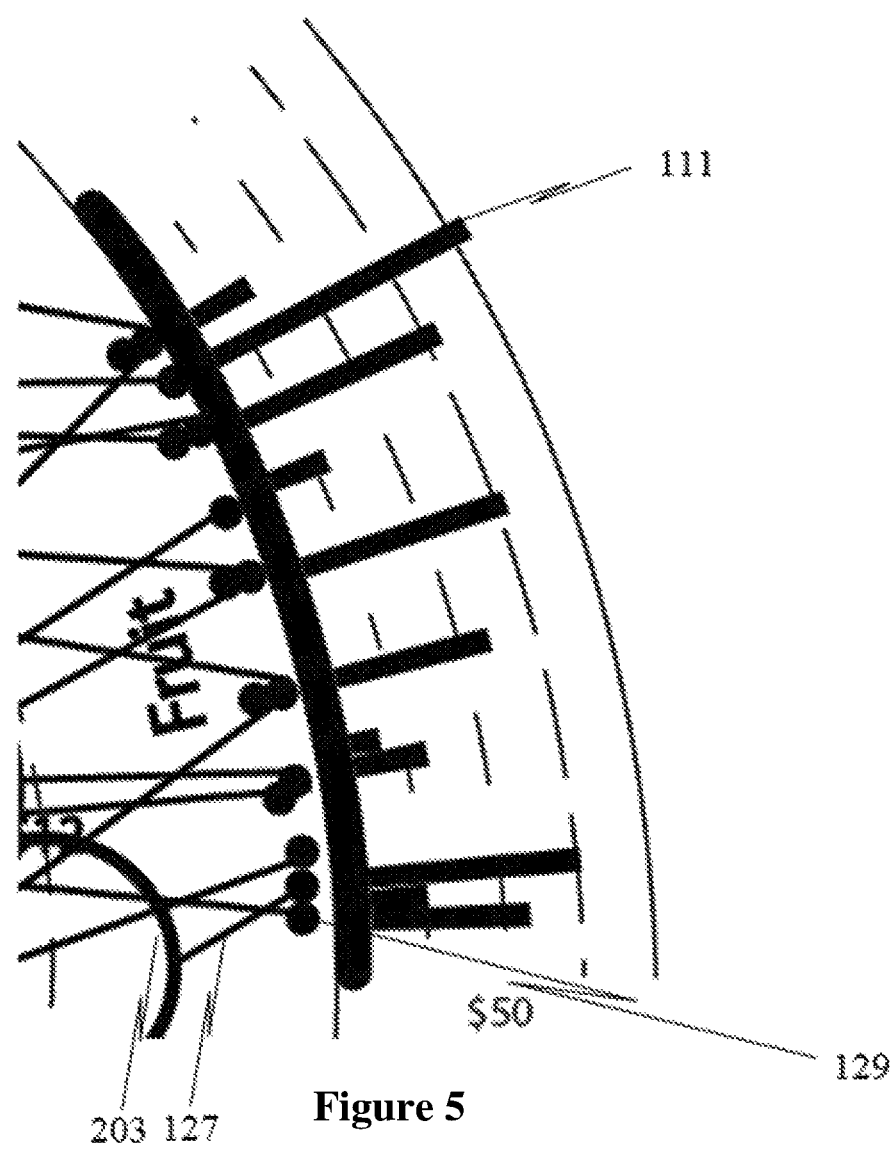
FIGS. 5 to 10 show detailed views of various elements of the graphical representations of FIGS. 1, 2 and 3.

FIG. 5 shows a close up view of the component icons (radial bars) 111 that represent each of the ingredients and sum of the selected BPD associated with the component selected (cost) for the menu in question. Also shown are the interconnecting lines 127 that connect between the component indicator icons 129 (ingredient dot) and menu item icons 203.

Figure 6:
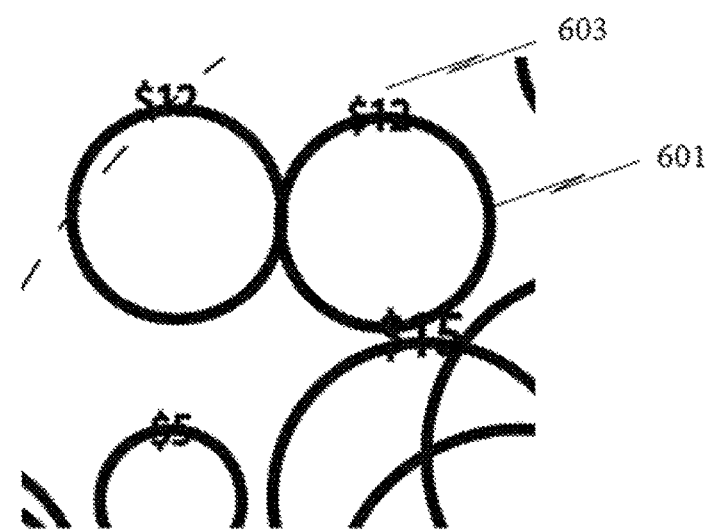

FIG. 6 shows a close up view of a menu item icon 601 along with a BPD value ($12) 603 associated with the selected BPD.

Figure 7:
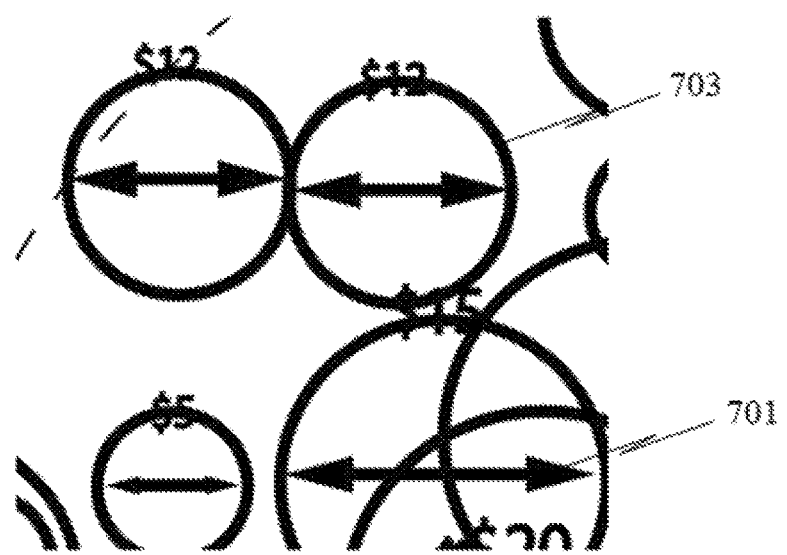

FIG. 7 shows a graphical indication of how the diameter (or radius) 701 of the menu item icons 703 can vary depending on the value of the selected BPD. That is, the menu item icon representing the BPD value $12 has a smaller diameter than the menu item icon that represents the BPD value $15.

Figure 8:
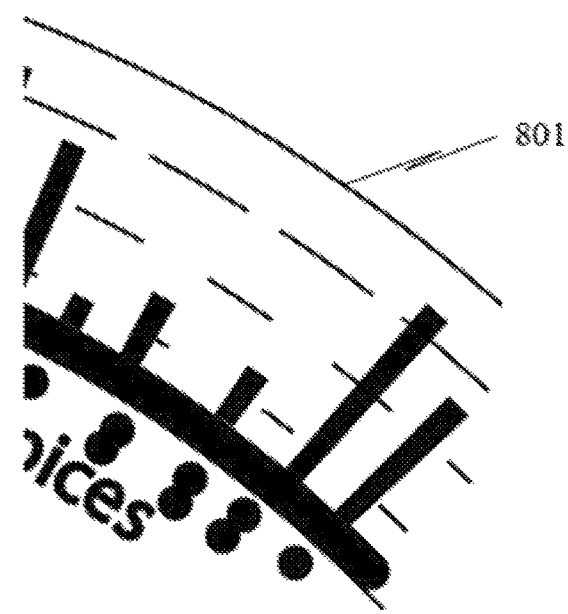

FIG. 8 shows a close up view of the concentric circles 801 (117, 119, 121, 123) that are used to indicate the value of each of the ingredients for the menu selected.

Figure 9:
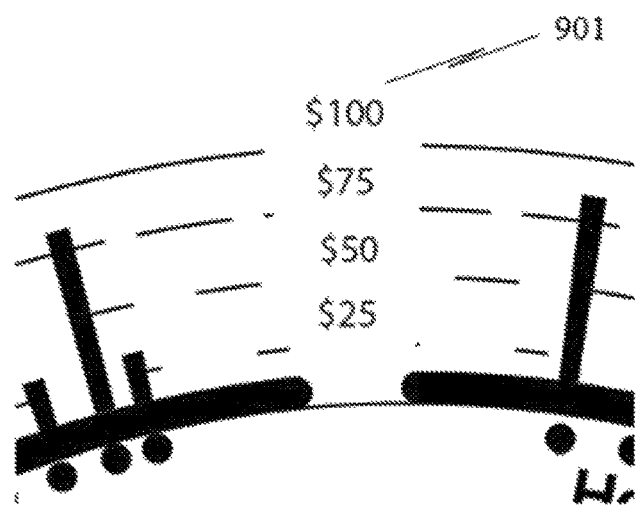

FIG. 9 shows a close up view of the representative value scale 901 (113) in text form for each ingredient.

Figure 10:
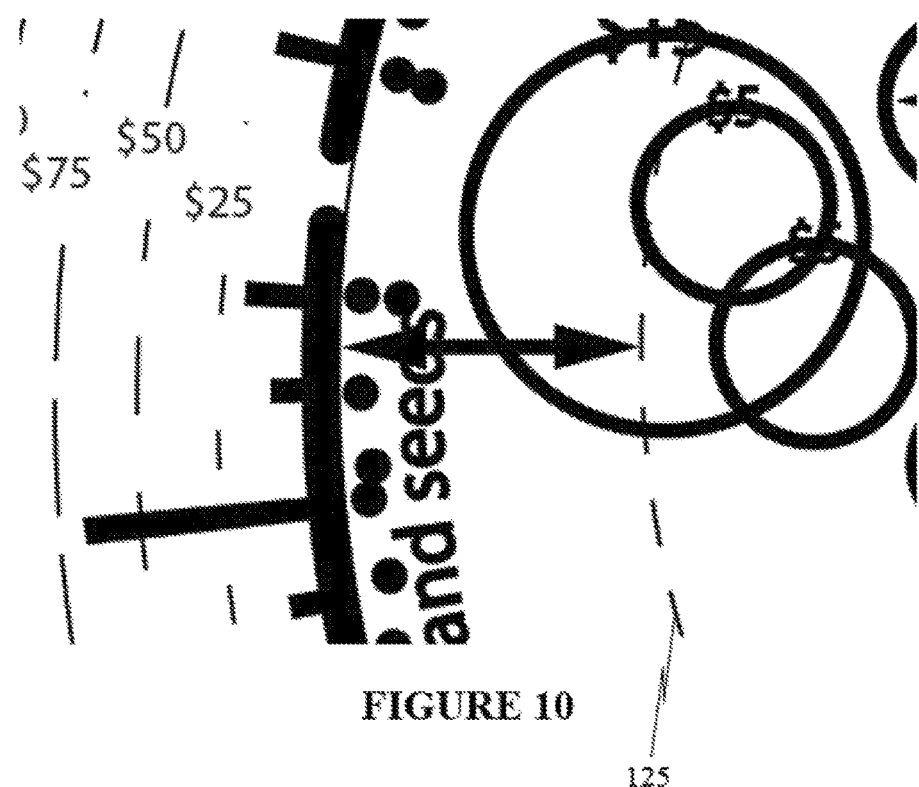

FIG. 10 shows a graphical indication of how the inner section circumference (maximum radius bar) 125 may be adjusted depending on the size of the largest and outermost menu item circle.

Further Embodiments

It will be understood that the embodiments of the present invention described herein are by way of example only, and that various changes and modifications may be made without departing from the scope of invention.

It will be understood that the method steps described above may be implemented using any suitable tool. For example, the method may be implemented using software code developed to perform the described methods. Alternatively, the method may be implemented using a programmed chip set arranged to perform the method steps. For example, the chip set may form part of a printing device specifically arranged to carry out the method of producing the herein visualizations. The chip set may be a hardwired chip set, programmable chip set, or software controlled chip set. Further, a hard wired or programmable computer system may be used to carry out the method steps. The computer system may be a computer system designed specifically for implementing this invention, or it may be a general purpose computer system that is specifically adapted, by way of software programming or chip set adaptation to perform the herein described methodology.

It will be understood that in certain embodiments the system may represent negative values in order to fully visualize the data concerned. These negative values may be shown as black (transparent) icons on a grey (mid tone) background, or could be represented as a different shape, for example. Also, negative values could be represented around the outer circle by a positive negative bar graph.

Figure 12:
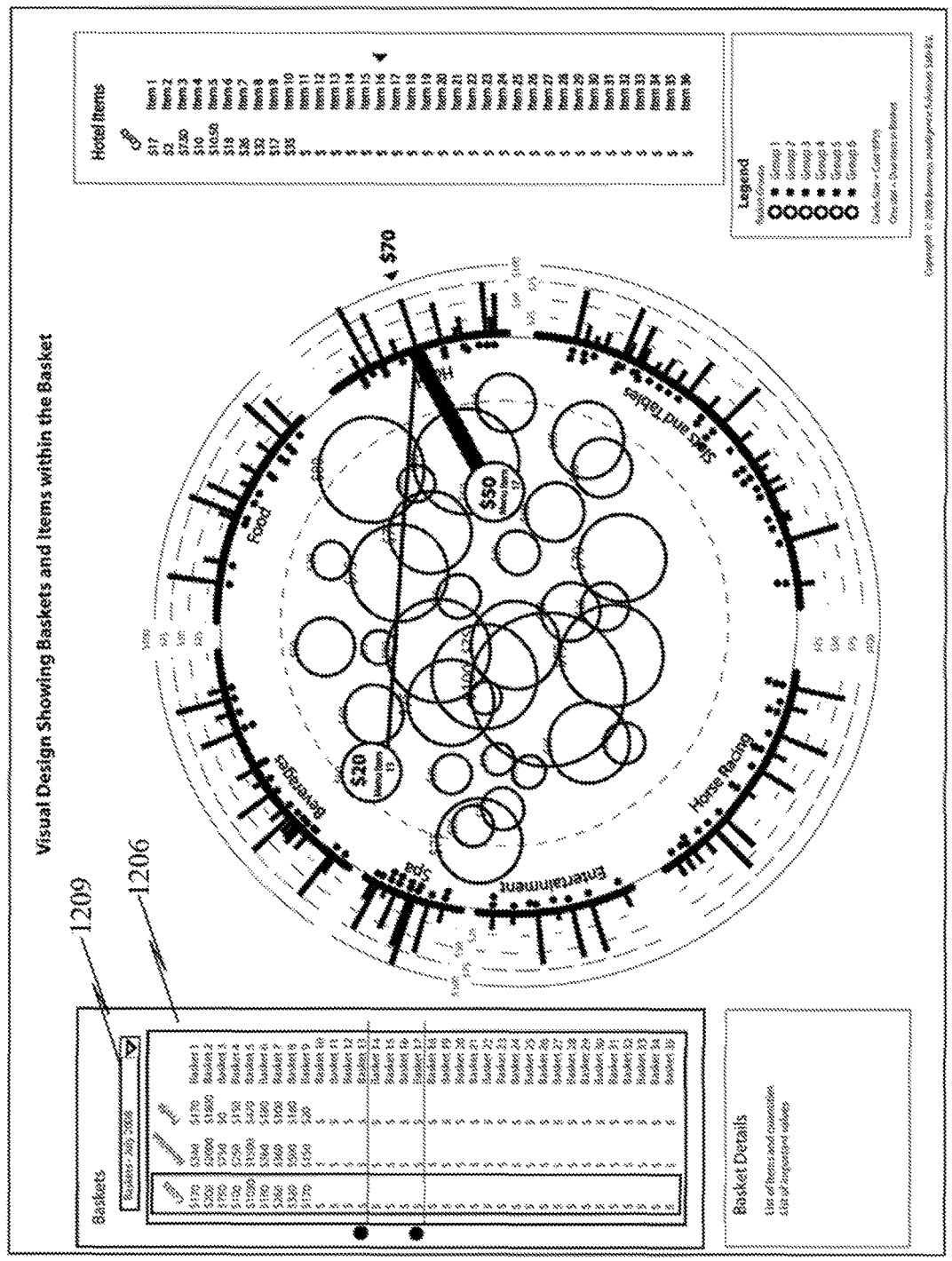
FIGS. 12 and 13 show a graphical representation of component analysis as used on hotel related market basket components according to an embodiment of the present invention.

Referring to FIG. 12, an alternative embodiment is described. In this embodiment, the data visualized is market basket data for a casino environment. The same principles of visualizing component data as described above also apply to this embodiment.

Figure 14:
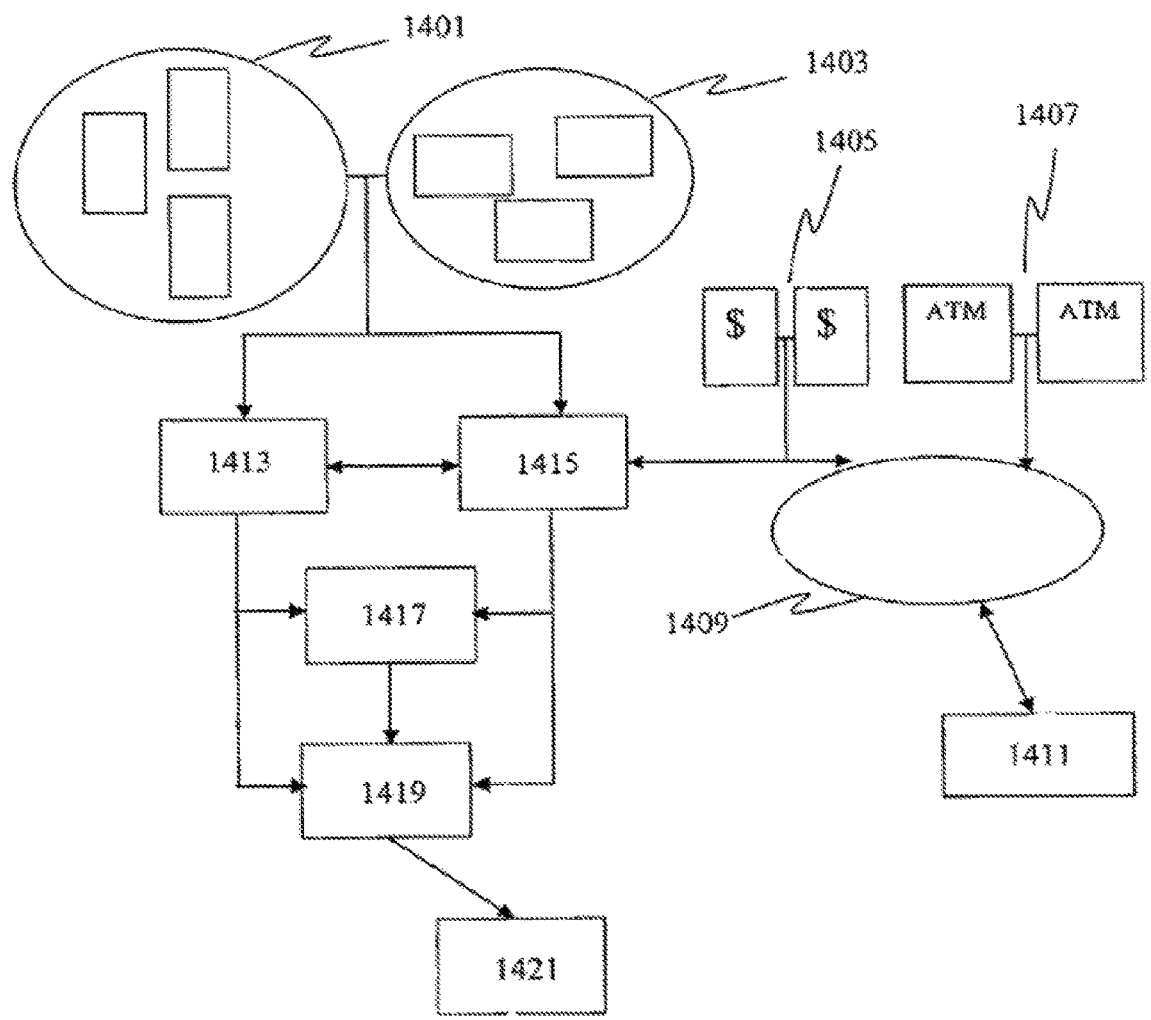
FIG. 14 shows a gaming environment system for use according to an embodiment of the present invention.

According to this embodiment, the above described system is installed as part of a gaming environment as shown in FIG. 14.

FIG. 14 shows an example of how the herein described system may be incorporated within a gaming environment. The gaming environment consists of a number of gaming machines 1401 and electronic tables 1403 (among other electronic gaming devices) that are adapted to communicate electronically with other systems using any suitable protocols, such as data packet protocols.

The gaming environment further includes a number of electronic cashier devices 1405 and ATMs 1407 which are in communication via a Wide Area Network 1409 with one or more financial databases 1411.

Data from the gaming machines 1401 and electronic tables 1403 are transferred to a reward program database 1413 and customer database 1415. It will be understood that these two databases may be combined into a single database.

Data from the cashier devices are also transferred to the reward program database 1413 and customer database 1415. The databases 1413 and 1415 are in communication with a central hotel management system 1417 that oversees the operation of the gaming environment, including the activities of customers in other areas of a casino, such as shops, hotels, spas etc.

The system 1419 described herein is in communication with the reward program database 1413, customer database 1415 and central hotel management system 1417 so the system can retrieve all necessary data about the activities within the gaming environment. The various embodiments as described herein are employed by the system 1419 to provide an output 1421.

Baskets of data for a particular time period are retrieved from the described gaming system. The baskets of data are selected by the user in the basket menu 1206 from a drop down menu 209. For example, the data may relate to a period of one month, such as July 2008.

Each basket of data is measured data retrieved from a gaming environment as described above. For example, the data may be associated with customers that have stayed or visited the gaming environment. The data may be collected by one or more suitable systems, such as systems that track customers through the use of banking cards, reward schemes, audio and visual detection systems, loyalty schemes, etc.

A list of BPDs is displayed and is selectable in the same manner as described in the above embodiments. In the same manner, components in the form of hotel items, as opposed to ingredients in FIG. 2B, are graphically visualized, and the selected BPD for the market basket is graphically indicated for each of the hotel items.

Figure 13:
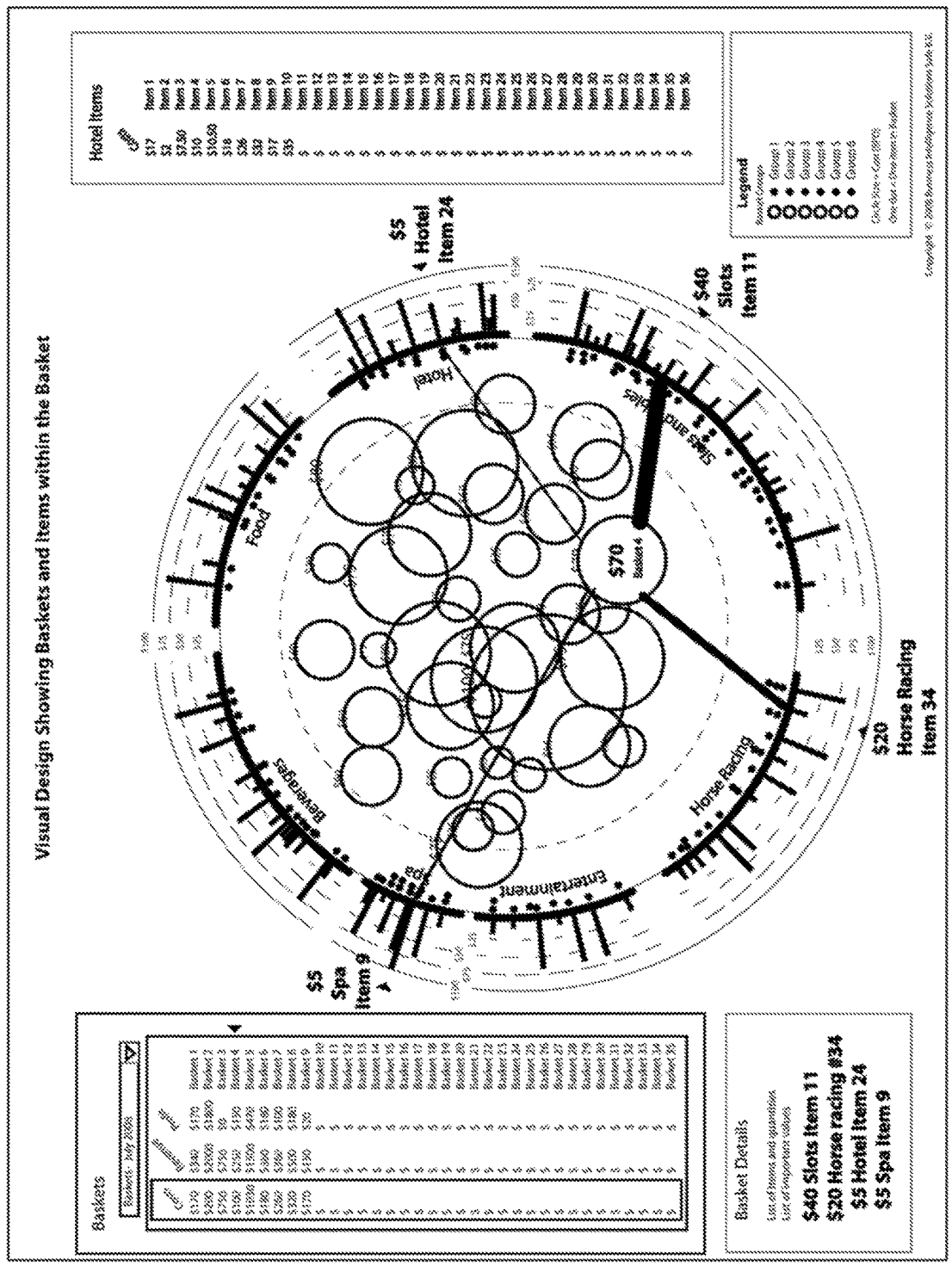

Also, referring to FIG. 13, the hotel item detail may be visualized in the same manner as that described in relation to, and as shown in, FIG. 3 for the above embodiment.

In a further embodiment, the data being visualized may be financial information associated with a business environment, for example. The financial information may be broken down into a number of different components and cross referenced with various different BPDs. For example, in a business environment, the costs, revenue or profit associated with a particular product or service can be listed and displayed as circles in the central visualization area. The various components that make up the production of the product or provision of the service can also be visualized in the same manner as the ingredients for menu items, or hotel items for a market basket. For example, the components may consist of raw materials, tax costs, utility costs, personnel costs, building costs, transport costs etc, where these are placed around the edge of the central visualization area. The selected BPD may then be represented for a selected product/service for a selected component, in the same manner as described above. Also, a relevant product/service may be indicated or represented for a selected component, in the same manner as described above.

According to a further embodiment, the arrangement of the grouped items (for example the menu item circles) in the central section, or the positioning of the components around the periphery, may be replaced by a graphical representation of the relationship between each of the menu items (or other relevant data type) and the components (e.g. ingredients) by utilizing the principles of a self organizing map. That is a self organizing map may be used to minimize the statistical distance (or maximize correlation) between each of the elements.

In yet a further embodiment, the data visualized may be retrieved from a manufacturing environment. In this example component data is automatically retrieved from a bill of materials for a particular product, where that product is made from a number of different components. Data associated with the components and products may be retrieved from a data store and visualized according to the methods herein described. For example, the mean time between failure (MTBF) values of a number of components may be measured and placed into a number of categories according to how likely/quickly the component is going to fail. The components may also be categorized in other ways, such as according to the cost of the component, availability of the component, complexity of the component, etc. A number of products (rather than menus) may be listed in the item table for selection by a user. A number of BPDs associated with the products and components may also be retrieved, such as the cost, time to build, complexity, source, MTBF etc. In this way the same advantages as provided in other embodiments is also provided here in a manufacturing environment. For example, an engineer is able to easily visualize how individual components interact for various BPDs within a single product, and to easily visualize which component categories have the most effect (in terms of a selected BPD) on a product.

Therefore, the data visualization techniques described herein transform the raw data received into different visual arrangements to enable further or hidden information within the raw data to be visually represented in a manner that conveys the information to a user in an efficient manner.

Further, it will be understood that the visual representations produced by the herein described system are specifically adapted to enable the visual representation of complex data in order to convey useful information while minimizing the use of production printing materials or limiting the space in which the information may be conveyed. That is, by enabling the herein described system to produce a visual representation that has one or more characteristics as described to summarize a complex problem or complex data, a number of technical advantages are immediately provided. For example, the characteristics of the visual representation may include the limitation of the size of the visual representation, the use of a minimum amount of ink, or the creation of the representation using a minimal or bounded area space or minimum amount of time. These characteristics then may solve one or more problems such as the excessive consumption of consumable items by reducing the required consumption of consumables such as paper and ink resources, as well as reducing the energy required to produce the printouts of the visual representations or the displaying of the information on a display module due to the ability to provide the required information in a visual space of a smaller size.

What we claim is:

1. In a data visualization computing system implemented on an electronic computing device having a display, a method of creating a graphical representation of a plurality of components that are grouped in a plurality of component groups, wherein the component groups are formed based on two or more different group types and values of one or more selectable metrics are associated with the components, the method including the steps of:
   detecting a selection of the one or more metrics wherein at least one of the one or more metrics are selected by using user interface controls;
   retrieving metric values for the selected metric associated with components belonging to component groups of a first group type;
   determining a relative proportion of the retrieved metric values across components that are members of a second type component group;

graphically representing the first type component group using one or more first icons that are graphically represented as an arc, based on the retrieved metric values, and positioned within a section of the graphical representation based on the determined relative proportion and located on a common circumference;

graphically representing one or more second icons associated with each component of components belonging to the component groups of the first group type, and graphically representing the one or more second icons within the common circumference and further graphically representing a link between the second icons and the first icons;

graphically representing the components of the second type component groups around a periphery of the section of the graphical representation by graphically displaying one or more third icons, wherein the third icons are graphically represented based on the retrieved metric values and wherein the third icons are graphically represented based on a total value of the retrieved metric values associated with the component, further including the step of determining an order in which each third icon representing a component is positioned around the periphery based on a separate metric value;

graphically representing each second type component group using one or more fourth icons, and determining an order in which each fourth icon is positioned around a periphery of the section of the graphical representation based on the separate metric value;

detecting a selection of one of the first icons and graphically highlighting the relationships between the selected first icon and one or more second icons or detecting a selection of one of the second icons and graphically highlighting the relationships between the selected icon and one or more first icons; and displaying the graphical representation on the display, by:
 rendering a rendered output including the graphical representation showing relationships between the plurality of components that are grouped in the plurality of component groups and the highlighted relationships; and
 providing the rendered output to the display device and generating the graphical representation on the display device to allow a user to visualize the data.

2. The method of claim 1, wherein the first icons form at least a portion of a heatmap or a self organizing map.

3. The method of claim 1, wherein the section of the graphical representation is formed as one of a geometric shape, organic shape, and dodecagon spiral.

4. The method of claim 1, wherein the positions of the first icons are automatically limited for representation within a user adjustable area of the graphical representation.

5. The method of claim 1, wherein the retrieved metric values determine at least one of the shape, shading, color, height, or size of the first icon.

6. The method of claim 1, wherein the total value of the retrieved metric values determines at least one of the shape, shading, color, height, or size of each third icon.

7. The method of claim 1, wherein each third icon is at least one of a bar, text, number, letter, character, line, geometric shape, organic shape, image or object.

8. The method of claim 1, further including the step of graphically representing a normalized scale for the components of the second type component groups around the periphery, wherein the normalized scale is represented by a series of concentric lines and the lines have a line to space ratio based on a normalization value being represented.

9. The method of claim 1, wherein the step of determining the relative proportion includes determining a weighted distance calculation based on the values of the selected metric for members of the second type component group.

10. A data visualization system for creating a graphical representation of a plurality of components that are grouped in a plurality of component groups, wherein the component groups are formed based on two or more different group types, and values of one or more selectable metrics are associated with the components, the system including:
 a processor;
 a memory device;
 a display device;
 a selection detection module executable by the processor arranged to detect a selection of the one or more metrics wherein at least one of the one or more metrics are selected by using user interface controls;
 a data retrieval module executable by the processor arranged to retrieve metric values for the selected metric associated with components belonging to component groups of a first group type from a data storage module in communication with the component data visualization system;
 a placement module executable by the processor arranged to determine a relative proportion of the retrieved metric values across components that are members of a second type component group; and further arranged to instruct an icon module executable by the processor to graphically represent the first type component group using one or more first icons as an arc that are graphically represented based on the retrieved metric values, and position the first icon within a section of the graphical representation based on the determined relative proportion, and located on a common circumference, and further arranged to instruct an icon module executable by the processor to graphically represent one or more second icons associated with each component of components belonging to the component groups of the first group type within the common circumference and further graphically representing a link between the second icons and the first icons, the placement module executable by the processor further arranged to instruct an icon module executable by the processor to graphically represent the components of the second type component groups around a periphery of the section of the graphical representation by graphically displaying one or more third icons, wherein the third icons are graphically represented based on the retrieved metric values and wherein the third icons are graphically represented based on a total value of the retrieved metric values associated with the component, the placement module executable by the processor further arranged to determine an order in which each third icon representing a component is positioned around the periphery based on a separate metric value, and the placement module executable by the processor further arranged to instruct an icon module executable by the processor to graphically represent each second type component group using one or more fourth icons, the placement module executable by the processor further arranged to determine an order in which each fourth icon is positioned around a periphery of the section of the graphical representation based on the separate metric value; and
 the selection detection module executable by the processor further arranged to detect a selection of one of the first icons and further instruct the icon module executable by the processor to graphically highlight a relationship between the selected first icon and one or more second icons or the selection detection module executable by the processor further arranged to detect a selection of one of the second icons and further instruct the icon module executable by the processor to graphically highlight a relationship between the selected icon and one or more first icons;

wherein the icon module executable by the processor to graphically represent the graphical representation on the display device, is further arranged to:

render a rendered output including the graphical representation showing relationships between the plurality of components that are grouped in the plurality of component groups and the highlighted relationships; and provide the rendered output to the display device and generate the graphical representation on the display device to allow a user to visualize the data.

11. The data visualization system of claim 10, wherein the first icons form at least a portion of a heatmap or a self organizing map.

12. The data visualization system of claim 10, wherein the section of the graphical representation is formed as one of a geometric shape, organic shape, and dodecagon spiral.

13. The data visualization system of claim 10, wherein the positions of the first icons are automatically limited for representation within a user adjustable area of the graphical representation.

14. The data visualization system of claim 10, wherein the retrieved metric values determine at least one of the shape, shading, color, height, or size of the first icon.

15. The data visualization system of claim 10, wherein the total value of the retrieved metric values determines at least one of the shape, shading, color, height, or size of each third icon.

16. The data visualization system of claim 10, wherein each third icon is at least one of a bar, text, number, letter, character, line, geometric shape, organic shape, image or object.

17. The data visualization system of claim 10, wherein the placement module executable by the processor is further arranged to instruct an icon module executable by the processor to graphically represent a normalized scale for the components of the second type component groups around the periphery, wherein the normalized scale is represented by a series of concentric lines and the lines have a line to space ratio based on a normalization value being represented.

18. The data visualization system of claim 10, wherein determining the relative proportion includes determining a weighted distance calculation based on the values of the selected metric for members of the second type component group.

* * * * *